(12) United States Patent
Langer et al.

(10) Patent No.: US 12,727,827 B2
(45) Date of Patent: Sep. 8, 2026

(54) GASTRIC RESIDENT ELECTRONICS

(71) Applicants: Massachusetts Institute of Technology, Cambridge, MA (US); The Brigham and Women's Hospital, Inc., Boston, MA (US)

(72) Inventors: Robert S. Langer, Newton, MA (US); Carlo Giovanni Traverso, Newton, MA (US); Yong Lin Kong, Salt Lake City, UT (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 230 days.

(21) Appl. No.: 18/316,954

(22) Filed: May 12, 2023

(65) Prior Publication Data

US 2023/0380768 A1 Nov. 30, 2023

Related U.S. Application Data

(62) Division of application No. 16/202,647, filed on Nov. 28, 2018, now Pat. No. 11,684,315.

(Continued)

(51) Int. Cl.

*A61B 5/00* (2006.01)
*A61B 5/07* (2006.01)
*A61M 31/00* (2006.01)

(52) U.S. Cl.

CPC .......... *A61B 5/6885* (2013.01); *A61B 5/0031* (2013.01); *A61B 5/073* (2013.01);

(Continued)

(58) Field of Classification Search

CPC ..... A61B 5/6885; A61B 5/0031; A61B 5/073; A61B 5/4238; A61B 5/6861;

(Continued)

(56) References Cited

U.S. PATENT DOCUMENTS 4,844,076 A 7/1989 Lesho et al.
5,002,772 A * 3/1991 Curatolo ............. A61K 9/2072 424/464

(Continued)

FOREIGN PATENT DOCUMENTS

CN 102370453 A 3/2012
WO WO 2005/079384 A2 9/2005

(Continued)

OTHER PUBLICATIONS

International Search Report and Written Opinion mailed Feb. 19, 2019, for Application No. PCT/US2018/062728.

(Continued)

*Primary Examiner* — Jacqueline Cheng
*Assistant Examiner* — Tho Q Tran
(74) *Attorney, Agent, or Firm* — Wolf, Greenfield & Sacks, P.C.

(57) ABSTRACT

Gastric resident electronics, devices, systems, and related methods are generally provided. Some embodiments comprise administering (e.g., orally) an (electronic) resident structure to a subject (e.g., a patient) such that the (electronic) resident structure is retained at a location internal to the subject for a particular amount of time (e.g., at least about 24 hours) before exiting said location internal to the subject. In some embodiments, the resident structure is a gastric resident electronic. That is to say, in some embodiments, the resident structure is configured for relatively long gastric residence and comprises an electronic component. In some embodiments, the structures and components (Continued)

described herein may comprise one or more components configured for the delivery of an active substance(s) (e.g., a pharmaceutical agent) to the subject. In some embodiments, the device has a modular design, combining an electronic component(s) with materials configured for controlled and/or tunable degradation/dissolution to determine the time at which (gastric) residence is lost and the device exits the location internal to the subject. For example, in some embodiments, the resident structure comprises an electronic component and one or more additional components associated with the electronic component such that the resident structure is configured to be retained at a location internal to a subject for greater than or equal to 24 hours.

23 Claims, 13 Drawing Sheets

Related U.S. Application Data

(60) Provisional application No. 62/591,556, filed on Nov. 28, 2017.

(52) U.S. Cl.
CPC .......... *A61B 5/4238* (2013.01); *A61B 5/6861* (2013.01); *A61B 5/6871* (2013.01); *A61M 31/002* (2013.01); *A61B 2560/0443* (2013.01); *A61B 2562/0285* (2013.01); *A61B 2562/162* (2013.01); *A61M 2205/0216* (2013.01); *A61M 2205/0272* (2013.01); *A61M 2205/3523* (2013.01); *A61M 2210/1053* (2013.01)

(58) Field of Classification Search
CPC .......... A61B 5/6871; A61B 2560/0443; A61B 2562/0285; A61B 2562/162; A61M 31/002; A61M 2205/0216; A61M 2205/0272; A61M 2205/3523; A61M 2210/1053
See application file for complete search history.

(56) References Cited

U.S. PATENT DOCUMENTS 5,318,557 A 6/1994 Gross
5,792,048 A 8/1998 Schaefer
6,804,558 B2 10/2004 Haller et al.
7,039,453 B2 5/2006 Mullick et al.
7,253,716 B2 8/2007 Lovoi et al.
8,036,731 B2 10/2011 Kimchy et al.
8,048,169 B2 11/2011 Burnett et al.
8,125,516 B2 2/2012 Iddan et al.
8,836,513 B2 9/2014 Hafezi et al.
9,270,025 B2 * 2/2016 Robertson ................ H01Q 1/08
9,985,320 B2 5/2018 Bettinger et al.
10,521,561 B1 * 12/2019 Euliano .................. A61B 5/065
11,684,315 B2 6/2023 Langer et al.
11,992,552 B2 * 5/2024 Bellinger ........... C08G 18/4277
2001/0051766 A1 12/2001 Gazdzinski
2005/0055039 A1 3/2005 Burnett et al.
2006/0122954 A1 6/2006 Podlasek
2007/0123809 A1 * 5/2007 Weiss .................... A61B 5/073 601/84
2010/0137686 A1 6/2010 Meron et al.
2011/0257491 A1 10/2011 Robertson et al.
2013/0310664 A1 11/2013 Kozloski et al.
2015/0051589 A1 2/2015 Sako et al.
2015/0118526 A1 4/2015 Bettinger et al.
2016/0367790 A1 * 12/2016 Belenky ................. A61B 5/073
2020/0281851 A1 9/2020 Grant et al.

FOREIGN PATENT DOCUMENTS

WO WO 2009/063375 A1 5/2009
WO WO 2013/145855 A1 12/2015
WO WO2015/191920 * 12/2015
WO WO 2015/191920 A1 12/2015
WO WO 2018/102799 A1 6/2018

OTHER PUBLICATIONS

International Preliminary Report on Patentability for International Application No. PCT/US2018/062728, mailed Jun. 11, 2020.

Abid, Ingestible Electronics Without Batteries: Wireless Power and Communication for Gastroresident Devices. 2016 MIT Master's Thesis. Department of Electrical Engineering and Computer Science, Massachusetts Institute of Technology, Available to the public after Feb. 22, 2017, 84 pages.

Abid et al., Wireless power transfer to millimeter-sized gastrointestinal electronics validated in swine model. Sci Rep. Apr. 27, 2017;7:46745(1-6). doi: 10.1038/srep46745.

Agrawal et al., Conformal phased surfaces for wireless powering of bioelectronic microdevices. Nat Biomed Eng. 2017;1:0043 (1-9). doi: 10.1038/s41551-017-0043. Epub Mar. 6, 2017.

Anderson, Mechanisms of inflammation and infection with implanted devices. Ch. 4 in Cardiovasc Pathol. Jul.-Sep. 1993;2(3)(Suppl):33s-41s.

Aoyagi et al., Gastric emptying of tablets and granules in humans, dogs, pigs, and stomach-emptying-controlled rabbits. J Pharm Sci. Dec. 1992;81(12):1170-4.

Awasthi et al., Decades of research in drug targeting to the upper gastrointestinal tract using gastroretention technologies: where do we stand? Drug Deliv. 2016;23(2):378-394. doi: 10.3109/10717544.2014.936535. Epub Jul. 15, 2014.

Bellinger et al., Oral, ultra-long-lasting drug delivery: Application toward malaria elimination goals. Sci Transl Med. Nov. 16, 2016;8(365):365ra157(1-12).

Benabid et al., Deep brain stimulation of the subthalamic nucleus for the treatment of Parkinson's disease. Lancet Neurol. Jan. 2009;8(1):67-81. doi: 10.1016/S1474-4422(08)70291-6.

Bettinger et al., Materials advances for next-generation ingestible electronic medical devices. Trends Biotechnol. Oct. 2015;33(10):575-585. doi: 10.1016/j.tibtech.2015.07.008. Epub Sep. 21, 2015.

Cassilly et al., Gastric emptying of a non-digestible solid: assessment with simultaneous SmartPill pH and pressure capsule, antroduodenal manometry, gastric emptying scintigraphy. Neurogastroenterol Motil. Apr. 2008;20(4):311-9. doi: 10.1111/j.1365-2982.2007.01061.x. Epub Jan. 13, 2008.

Dagdeviren et al., Miniaturized neural system for chronic, local intracerebral drug delivery. Sci Transl Med. Jan. 24, 2018;10(425):eaan2742(1-10). doi: 10.1126/scitranslmed.aan2742.

Darouiche, Treatment of infections associated with surgical implants. Engl J Med. Apr. 1, 2004;350(14):1422-9.

De Bakey et al., Bezoars and concretions: Comprehensive review of literature, with analysis of 303 collected cases and presentation of eight additional cases. Part 1. Surgery. Dec. 1938;4(6):934-63.

Del Pozo et al., Clinical practice. Infection associated with prosthetic joints. Engl Med. Aug. 20, 2009;361(8):787-94. doi: 10.1056/NEJMcp0905029.

Eilenberg et al., Control of a powered ankle-foot prosthesis based on a neuromuscular model. IEEE Trans Neural Syst Rehabil Eng. Apr. 2010;18(2):164-73. doi: 10.1109/TNSRE.2009.2039620. Epub Jan. 12, 2010.

Eng et al., Gastrointestinal bezoars: history and current treatment paradigms. Gastroenterol Hepatol (N Y). Nov. 2012;8(11):776-8.

Evans et al., Measurement of gastrointestinal pH profiles in normal ambulant human subjects. Gut. Aug. 1988;29(8):1035-41.

Farra et al., First-in-human testing of a wirelessly controlled drug delivery microchip. Sci Transl Med. Feb. 22, 2012;4(122):122ra21(1-10). doi: 10.1126/scitranslmed.3003276. Epub Feb. 16, 2012.

Gao et al., Fully integrated wearable sensor arrays for multiplexed in situ perspiration analysis. Nature. Jan. 28, 2016;529(7587):509-514. Suppl Info . doi: 10.1038/nature16521.

(56) References Cited

OTHER PUBLICATIONS

Ghosh et al., Addressing unmet clinical needs with 3D printing technologies. Adv Healthc Mater. Sep. 2018;7(17):1800417(1-24). doi: 10.1002/adhm.201800417. Epub Jul. 13, 2018.
Gordi et al., Pharmacokinetics of gabapentin after a single day and at steady state following the administration of gastric-retentive-extended-release and immediate-release tablets: a randomized, open-label, multiple-dose, three-way crossover, exploratory study in healthy subjects. Clin Ther. May 2008;30(5):909-16. doi: 10.1016/j.clinthera.2008.05.008.
Gorter et al., Management of trichobezoar: case report and literature review. Pediatr Surg Int. May 2010;26(5):457-63. doi: 10.1007/s00383-010-2570-0. Epub Mar. 6, 2010.
Grayson et al., Multi-pulse drug delivery from a resorbable polymeric microchip device. Nat Mater. Nov. 2003;2(11):767-72. Epub Oct. 19, 2003.
Hafezi et al., An ingestible sensor for measuring medication adherence. IEEE Trans Biomed Eng. Jan. 2015;62(1):99-109.
Iddan et al., Wireless capsule endoscopy. Nature. May 25, 2000;405(6785):417-418.
Imaz et al., Safety and effectiveness of the intragastric balloon for obesity. A meta-analysis. Obes Surg. Jul. 2008;18(7):841-6. doi: 10.1007/s11695-007-9331-8. Epub May 6, 2008.
Kalantar-Zadeh et al., A human pilot trial of ingestible electronic capsules capable of sensing different gases in the gut. Nat Electron. Jan. 2018;1:79-87.
Kim et al., Epidermal electronics. Science. Aug. 12, 2011;333(6044):838-843. Erratum 1pg. doi: 10.1126/science.1206157.
Kirschenbaum et al., Heartfelt Swallow: Management of a Case of Multiple Ingested Foreign Bodies. Sep. 2017. Crsls Mis Case Report from SLS.org, e2017.0004 (1-5).
Kirtane et al., Development of an oral once-weekly drug delivery system for HIV antiretroviral therapy. Nat Commun. Jan. 9, 2018;9(2):1-12. doi: 10.1038/s41467-017-02294-6.
Klug et al., Risk factors related to infections of implanted pacemakers and cardioverter-defibrillators: results of a large prospective study. Circulation. Sep. 18, 2007;116(12):1349-55. Epub Aug. 27, 2007.
Kong et al., 3D-printed gastic resident electronics. Adv Mater Technol. 2019;1800490(1-11). doi: 10.1002/admt.201800490.
Laulicht et al., Understanding gastric forces calculated from high-resolution pill tracking. Proc Natl Acad Sci U S A. May 4, 2010;107(18):8201-6. doi: 10.1073/pnas.1002292107. Epub Apr. 19, 2010.
Laulicht et al., Simple battery armor to protect against gastrointestinal injury from accidental ingestion. Proc Natl Acad Sci U S A. Nov. 18, 2014;111(46):16490-5. doi: 10.1073/pnas.1418423111. Epub Nov. 3, 2014.
Lavine et al., If I only had a . . . Science Feb. 8, 2002;295(5557):995.
Lee et al., Implantable batteryless device for on-demand and pulsatile insulin administration. Nat Commun. Apr. 13, 2017;8:15032(1-10). doi: 10.1038/ncomms15032.
Liu et al., Triggerable tough hydrogels for gastric resident dosage forms. Nat Commun. Jul. 25, 2017;8(1):124(1-10). doi: 10.1038/s41467-017-00144-z.
Mandal et al., Gastro-retentive drug delivery systems and their in vivo success: A recent update. Asian J Pharm Sci. Oct. 2016; 11(5): 575-84.
Maqbool et al., Wireless capsule motility: comparison of the SmartPill GI monitoring system with scintigraphy for measuring whole gut transit. Dig Dis Sci. Oct. 2009;54(10):2167-74. doi: 10.1007/s10620-009-0899-9. Epub Aug. 5, 2009.
Medani et al., Small bowel obstruction secondary to migration of a fragment of lithobezoar: a case report. Cases J. Dec. 7, 2009;2:9155(1-3). doi: 10.1186/1757-1626-2-9155.
Mimee et al., An ingestible bacterial-electronic system to monitor gastrointestinal health. Science. May 25, 2018;360(6391):915-918(1-4). doi: 10.1126/science.aas9315.
Mintchev et al., Pilot study of temporary controllable gastric pseudobezoars for dynamic non-invasive gastric volume reduction. Physiol Meas. Feb. 2010;31(2):131-44. doi: 10.1088/0967-3334/31/2/001. Epub Dec. 11, 2009.
Moore et al., Beyond cochlear implants: awakening the deafened brain. Nat Neurosci. Jun. 2009;12(6):686-91. doi: 10.1038/nn.2326. Epub May 26, 2009.
Nadeau et al., Prolonged energy harvesting for ingestible devices. Nat Biomed Eng. 2017;1:0022(1-8). doi: 10.1038/s41551-016-0022. Epub Feb. 6, 2017.
Nathan et al., An implantable synchronous pacemaker for the long term correction of complete heart block. Am J Cardiol. Mar. 1963;11(3):362-7.
Phillips et al., Gastric trichobezoar: case report and literature review. Mayo Clin Proc. Jul. 1998;73(7):653-6.
Prausnitz et al., Transdermal drug delivery. Nat Biotechnol. Nov. 2008;26(11):1261-8. doi: 10.1038/nbt.1504.
Prescott et al., Chronic, programmed polypeptide delivery from an implanted, multireservoir microchip device. Nat Biotechnol. Apr. 2006;24(4):437-8. Epub Mar. 12, 2006.
Reefhuis et al., Risk of bacterial meningitis in children with cochlear implants. N Engl J Med. Jul. 31, 2003;349(5):435-45.
Salessiotis, Measurement of the diameter of the pylorus in man. I. Experimental project for clinical application. Am J Surg. Sep. 1972;124(3):331-3.
Santini et al., A controlled-release microchip. Nature. Jan. 28, 1999;397(6717):335-8.
Sarna et al., Gastric pacemakers. Gastroenterology. Feb. 1976;70(2):226-31.
Schierholz et al., Implant infections: a haven for opportunistic bacteria. J Hosp Infect. Oct. 2001;49(2):87-93.
Schork, Personalized medicine: Time for one-person trials. Nature. Apr. 29, 2015;520(7549):609-11. doi: 10.1038/520609a. retrieved from the internet at http://www.nature.com/news/personalized-medicine . . . Apr. 30, 2015. 11 pages.
Silva et al., Implantable loop recorder monitoring for refining management of children with inherited arrhythmia syndromes. J Am Heart Assoc. May 26, 2016;5(6):003632(1-9). doi: 10.1161/JAHA.116.003632. accessed online at http://ahajournals.org.
Snoeck et al., Gastrointestinal transit time of nondisintegrating radio-opaque pellets in suckling and recently weaned piglets. J Control Release. Jan. 8, 2004;94(1):143-53.
Stack et al., Pharmacobezoar: an evolving new entity. Dig Dis. Nov.-Dec. 1995;13(6):356-64.
Traverso et al., Perspective: Special delivery for the gut. Nature. Mar. 26, 2015;519(7544):S19. doi: 10.1038/519S19a.
Tripathi et al., Current State and Future Perspectives on Gastroretentive Drug Delivery Systems. Pharmaceutics. Apr. 20, 2019;11(4):193.
Tsesmeli et al., Review of endoscopic devices for weight reduction: old and new balloons and implantable prostheses. Endoscopy. Dec. 2009;41(12):1082-9. doi: 10.1055/s-0029-1215269. Epub Nov. 6, 2009.
Uhrich et al., Polymeric systems for controlled drug release. Chem Rev. Nov. 10, 1999;99(11):3181-98.
Van Der Schaar et al., A novel ingestible electronic drug delivery and monitoring device. Gastrointest Endosc. Sep. 2013;78(3):520-8. doi: 10.1016/j.gie.2013.03.170. Epub May 14, 2013.
Veiseh et al., Size- and shape-dependent foreign body immune response to materials implanted in rodents and non-human primates. Nat Mater. Jun. 2015;14(6):643-51. doi: 10.1038/nmat4290. Epub May 18, 2015. Suppl Info, 1 pg.
Waltz, Drugs go wireless. Nat Biotechnol. Jan. 2016;34(1):15-8. doi: 10.1038/nbt.3446.
Watson et al., Telemetering from within the body using a pressure-sensitive radio pill. Gut. Jun. 1962;3:181-6.
Zhang et al., A pH-responsive supramolecular polymer gel as an enteric elastomer for use in gastric devices. Nat Mater. Oct. 2015;14(10):1065-71. doi: 10.1038/nmat4355. Epub Jul. 27, 2015. Adv online publication, 9 pages.
Zrenner et al., Fighting blindness with microelectronics. Sci Transl Med. Nov. 6, 2013;5(210):210ps16(1-7). doi: 10.1126/scitranslmed.3007399.

(56) References Cited

OTHER PUBLICATIONS

Zworykin et al., A Radio Pill. Nature. May 4, 1957;179:898. 1 page.

* cited by examiner

GASTRIC RESIDENT ELECTRONICS

RELATED APPLICATIONS

This application is a divisional of U.S. patent application Ser. No. 16/202,647, filed Nov. 28, 2018, and entitled "GASTRIC RESIDENT ELECTRONICS," which claims priority under 35 U.S.C. § 119(e) to U.S. Provisional Application Ser. No. 62/591,556, filed Nov. 28, 2017, the contents of each of which are incorporated herein by reference in its entirety for all purposes.

STATEMENT OF GOVERNMENT SUPPORT

This invention was made with government support under EB000244 awarded by the National Institutes of Health. The government has certain rights in the invention.

FIELD OF THE INVENTION

Embodiments described herein generally relate to gastric resident electronics and related methods.

BACKGROUND OF THE INVENTION

Long-term implantation of biomedical electronics into the human body enables advanced diagnostic and therapeutic functionalities. However, most long-term resident electronics devices require invasive procedures for implantation as well as a specialized receiver for communication. Recent developments in ingestibles have noted a myriad of functionalities, incorporating temperature, pH, pressure, or biomolecular sensors, wireless identification microchip, gas sensor, camera for wireless imaging and endoscopy or drug delivery modules. However, these ingestible electronics are generally incapable of maintaining a stable long-residence in the stomach. Most demonstrations to date are limited to a passive, uncontrolled gastric residence, which limits the potential application of ingestible bio-electronics to transient diagnostics and therapeutic strategies.

Accordingly, improved system and methods are needed.

SUMMARY OF THE INVENTION

Gastric resident electronics, devices, systems, and related methods are generally provided.

In one aspect, methods are provided. In some embodiments, the method comprises administering orally, to a subject, a resident structure comprising an electronic component and allowing the resident structure to enter the stomach, retaining the resident structure in the stomach for a residence period of at least 24 hours and, during the residence period, transmitting a signal from the electronic component to a device external of the stomach and/or transmitting a signal from a device external of the stomach to the electronic component, at the end of the residence period, allowing the electronic component to pass from the stomach through the pylorus.

In some embodiments, the signal triggers the electronic component to release a pharmaceutical agent from the resident structure.

In some embodiments, the signal provides a physiological condition of the subject to the device external of the stomach.

In some embodiments, the signal mediates the exit of the electronic component from the stomach through the pylorus.

In some embodiments, the resident structure comprises a degradable component linked to the electronic component such that the degradable component mediates the exit of the electronic component from the stomach through the pylorus of the subject.

In some embodiments, the signal triggers the degradable component to dissolve, degrade, mechanically weaken, and/or mechanically separate from the electronic component such that the electronic component passes from the stomach through the pylorus.

In some embodiments, the signal triggers the electronic component to apply a voltage to the degradable component.

In some embodiments, the method comprises delivering an electronic component to a subject, comprising, administering orally, to a subject, a resident structure comprising an electronic component such that the electronic component is retained at a location internal to the subject for at least about 24 hours, wherein the resident structure comprises an elastic core, two or more polymeric arms associated with the elastic core, and the electronic component associated with the elastic core.

In some embodiments, the resident structure comprises a degradable linker.

In some embodiments, the method comprises removing the electronic component from the location internal to the subject by degrading the degradable linker.

In some embodiments, degrading the degradable linker comprises applying, via the electronic component, a voltage to the degradable linker.

In some embodiments, the degradable linker comprises a plurality of carbonaceous particles, carbon nanotubes, and/or conductive particles.

In some embodiments, the method comprises administering orally, to a subject, a resident structure comprising two or more arms and an electronic component associated with the two or more arms, wherein the resident structure is configured to be retained at a location internal to the subject for at least about 24 hours, determining, via the electronic component, a physiological condition of the subject at the location internal to the subject, and transmitting a signal comprising the physiological property of the subject, via the electronic component, to an extracorpeal receiver, wherein the location internal to the subject is proximate the pylorus.

In some embodiments, the method comprises administering orally, to a subject, a resident structure comprising two or more arms, an electronic component associated with the two or more arms, and a pharmaceutical agent associated with the electronic component, wherein the resident structure is configured to be retained at a location internal to the subject for at least about 24 hours, determining, via the electronic component, a physiological condition of the subject at the location internal to the subject; and releasing, at a particular physiological condition(s), at least a portion of the pharmaceutical agent, wherein the location internal to the subject is proximate the pylorus.

In another aspect, resident structures are provided. In some embodiments, the resident structure comprises an electronic component linked to a degradable component, wherein the resident structure has a first, compressed configuration in which it can be introduced to a subject orally and will pass to the stomach, a second, expanded configuration in which the resident structure is retained within the stomach and does not pass into the pylorus under normal physiological conditions, and a third configuration in which the degradable portion dissolves, degrades, mechanically weakens, and/or mechanically separates from the electronic component, and the electronic component passes from the stomach through the pylorus.

In some embodiments, the resident structure comprises a first elastic polymeric component, a second polymeric component coupled to the first elastic polymeric component, and an electronic component associated with the second polymeric component, wherein the resident structure has a folding force of at least about 0.2 N, wherein the resident structure has an uncompressed cross-sectional dimension of at least about 2 cm, and wherein the resident structure is configured such that it is retained at a location internally of a subject for at least about 24 hours.

In some embodiments, the resident structure comprises an elastic core, three or more polymeric arms associated with the elastic core, and a degradable linker coupling the elastic core and at least two of the three or more polymeric arms, wherein at least one of the three or more polymeric arms comprises an electronic component.

In some embodiments, the resident structure is configured for oral administration and comprises an elastic core, two or more polymeric arms associated with the elastic core, and an electronic component associated with the elastic core, wherein the resident structure is configured such that it is retained at a location internally of a subject for at least about 24 hours.

In some embodiments, the resident structure is configured for transmission of a signal extra-corporeally and comprises an electronic component comprising a wireless transmitter, the electronic component associated with an elastic core, wherein the resident structure is configured such that it is administered orally and retained at a location internal to a subject adjacent the pylorus of a subject for at least about 24 hours, and wherein the wireless transmitter is configured to transmit a signal from the location internal to the subject to a receiver positioned extracorporeal of the subject.

In some embodiments, the resident structure comprises a pharmaceutical agent associated with the electronic component.

In some embodiments, at least a portion of the pharmaceutical agent is configured to be released upon a signal received from the electronic component.

In some embodiments, the location internal to the subject is the stomach.

In some embodiments, the location internal to the subject is proximate the pylorus.

In some embodiments, the linker comprises a plurality of carbonaceous particles, carbon nanotubes, and/or conductive particles.

In some embodiments, the electronic component is configured to apply a voltage to the linker.

In some embodiments, the linker is configured to degrade in the presence of a voltage.

In some embodiments, the linker is configured to degrade in the presence of a generated increase in temperature.

In some embodiments, the linker degrades, dissolves, disassociates, or mechanically weakens in a gastric environment which results in loss of retention shape integrity and passage out of a gastric cavity.

In some embodiments, the polymeric arms are configured to maintain structural integrity during a residence period of the resident structure.

In some embodiments, the resident structure comprises a containing structure.

In some embodiments, the resident structure is constructed and arranged to have a first configuration when contained within the containing structure and a second configuration after release from the containing structure.

In some embodiments, the electronic component comprises a wireless transmitter.

In some embodiments, the electronic component comprises a pharmaceutical agent configured for release at the location internal to the subject.

In some embodiments, the resident structure is constructed and arranged to undergo elastic recoil upon release from the containing structure, the resident structure having a first configuration when contained within the containing structure and a second configuration after release from the containing structure.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

(FIG. 2A) patient-specific multi-material 3D printing of GRE. (FIG. 2B) GRE is designed to be delivered orally (1), reside in the stomach for weeks (2) and finally break up (3) pass through the pylorus and be excreted from the gastric space. Specifically, as shown in (FIG. 2C), the GRE can be compressed into a capsule-size dosage form. The expansion of the device as shown in (FIG. 2D) enables gastric residence and allows long-term remote communication with personal device. (FIG. 2E) Ultimately, the disintegration of the device allows the safe passage of the device from the gastric space. (FIG. 2F) GRE is directly compatible with personal devices, such as a smart phone, empowering the users to communicate and control the long-resident structure without a specialized equipment. (FIG. 2G) This enables a seamless interconnection with other wireless electronics peripherals, wearable devices and biomedical implants, allowing a real-time feedback-based automated treatment or responsive medication. The interconnection of GRE with the digital cloud via personal electronics could ultimately enable the next generation of digital medical interventions (FIG. 2H) Computer-aided design models of the gastric-resident electronics device showing the (i) gastric resident architecture; (ii) integration of electronics and power system for communications and control; (iii) personalized drug delivery modules. Inset shows the cross-section of the design demonstrating the integration of a Bluetooth wireless-microcontroller, antenna, batteries and drug delivery modules. (FIG. 2I) Optical photograph shows the dimension of a fabricated device. (FIG. 2J) X-ray image shows the deployed GRE in a porcine stomach.

(FIG. 3A) Schematic of the computer-aided-design model of the 3D printed multi-materials architecture. Left inset image shows the optical photograph of a 3D printed multi-material GRA and right inset is an X-ray image indicating the relative location of metal probes embedded in the GRA of the in vivo gastric residence study. (FIG. 3B) High speed camera imaging series showing the expansion of 3D printed architecture (i) before, (ii) during and (iii) after expansion. (FIG. 3C) X-ray image shows the gastric residence of a control prototype demonstrating the maximum gastric residence of four days without a gastric residence architecture. (FIG. 3D) In contrast, GRA permits gastric residence for up to 24 days, as shown in the X-ray image. The structure will subsequently disintegrate by detachment. First, one of the GRA arm is detached, as indicated by the metal probes at day 27. (The top inset image shows the detached arm that has been passed to the intestinal region, while the remaining structure stays in the gastric space.) Second, at day 30, both GRA arms are detached, allowing the GRA to pass between day 31 and day 33. (FIG. 3E) GRE exhibited a similar disintegration as GRA where at day 24, one of the prototypes began to lose one of the gastric resident structure, before both gastric residence arms are detached. (FIG. 3F) In another GRE, a maximum gastric residence of 36 days was achieved. (FIG. 3G) Statistical comparison of device residence period of a structure without GRA (control), GRA prototype and ultimately GRE, demonstrating the effectiveness of GRA in prolonging gastric residence.

(FIG. 4A) Average Received Signal Strength Indicator (RSSI) of seven devices measured with a smart phone. Inset shows an X-ray image of the integrated electronics at the GRE with three major components. (FIG. 4B) The RSSI measured from GRE in a porcine stomach. The distance is measured relative to the abdominal surface of the pig. The in vivo measurements are repeated in three orthogonal directions. Inset shows the stability of RSSI measured at fixed location. (FIG. 4C) *GRE bilateral wireless communications from the gastric space*: the change of temperature measured from GRE delivered to the porcine stomach, demonstrating the ability to perform bilateral wireless Bluetooth interconnection between the device in the gastric space and a smart phone. (FIG. 4D) *Prolonging GRE lifetime*: the optimization of communication protocol and power sources enable the maximum device lifetime of 20.1 days when configured to perform temperature measurement at an hourly interval. Inset shows bar charts demonstrate the average lifetime of GRE when maintained at three different mode of operation. The graph shows the in vitro experimental data of temperature measured when the device is left in a convection oven maintained at 37° C. over 19.5 days.

(FIG. 5A) The cumulative release of doxycycline in a controlled released poly(ε-caprolactone) matrix formulation (red dots and blue line), in comparison to the release profile of 20 mg in tablet form (blue stars and black line) and delayed released tablet (purple diamond and green line). (FIG. 5B) The cumulative release of levonorgestrel from a 3D printed formulation over one week, demonstrating the ability to integrate GRE with a controlled delivery platform. Inset shows the 3D printing of levonorgestrel into the defined drug wells. (FIG. 5C) In vivo long-residence performance of GRE: The graph shows the measured Received Signal Strength Indicator (RSSI) of a GRE deployed in a porcine stomach of a pig from tablets attached to the walls of the cage over 15.3 days. Inset shows an X-ray image of the GRE (yellow circled) inside the stomach at the day the device is deployed. (FIG. 5D) In vivo long-residence physiological parameter sensing with GRE: a direct, real-time core-temperature measurement with a tablet attached on the wall of the cage over 17 days. Inset shows the integrity of the GRE on day 15, demonstrating the robustness of the GRE to withstand the hostile gastric environment for weeks.

(FIG. 8A) Prior to triggering, the GRA is bonded to the "head" of GRE electronics with electroactive adhesive. (FIG. 8B) Upon triggering, the GRA is separated as the adhesive failed. (FIG. 8C) A slight movement of the separated structure shows that GRA was completed detached from the "head" of the GRE where the compression system (an embedded spring) of the device was exposed.

(FIG. 9B) The wireless triggered release of drug as a result of the opening of drug reservoir cover (arrow) which was not interfered by the mucous coverage. (FIG. 9C) Washed triggered reservoir to show the expanded system (arrow).

DETAILED DESCRIPTION

Figure 1A:
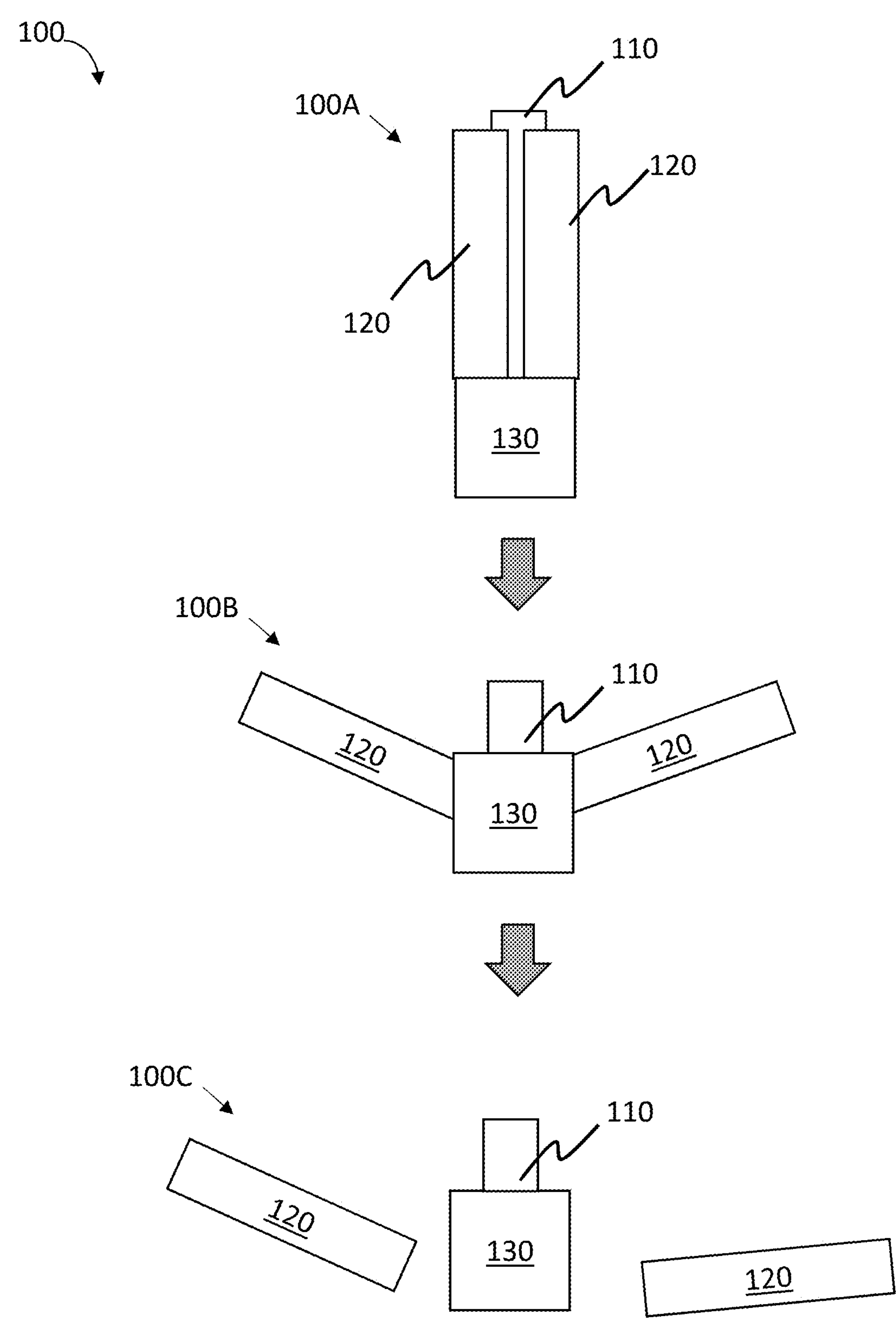
FIG. 1A is a schematic illustration of a gastric resident structure, according to one set of embodiments.

Gastric resident electronics, devices, systems, and related methods are generally provided. Some embodiments comprise administering (e.g., orally) an (electronic) resident structure to a subject (e.g., a patient) such that the (electronic) resident structure is retained at a location internal to the subject for a particular amount of time (e.g., at least about 24 hours) before exiting said location internal to the subject. In some embodiments, the resident structure is a gastric resident electronic. That is to say, in some embodiments, the resident structure is configured for relatively long gastric residence and comprises an electronic component. In some embodiments, the structures and components described herein may comprise one or more components configured for the delivery of an active substance(s) (e.g., a pharmaceutical agent) to the subject. Advantageously, the structures described herein exhibit stability in acidic environments, mechanical flexibility and strength proximate an internal orifice (e.g., pylorous of the subject), easy passage through the GI tract until residence at a desired location internal to the subject, and/or controllable/triggerable dissolution/degradation in a physiological environment (e.g., the gastrointestinal environment). In some embodiments, the device has a modular design, combining an electronic component(s) with materials configured for controlled and/or tunable degradation/dissolution to determine the time at which (gastric) residence is lost and the device exits the location internal to the subject. For example, in some embodiments, the resident structure comprises an electronic component and one or more additional components associated with the electronic component such that the resident structure is configured to be retained at a location internal to a subject for greater than or equal to 24 hours.

Advantageously, the structures and components described herein are configured for gastric residence of an electronic component at a location internal to a subject without the need for a surgical procedure (e.g., an incision, implantation within layers of tissue). In some cases, the resident structure may be administered to a subject. In some embodiments, the resident structure is administered orally, rectally, vaginally, nasally, or uretherally. In some embodiments, the resident structure is contained within a containing structure (e.g., during administration), as described in more detail below. In certain embodiments, upon reaching the location internal to the subject (e.g., in the gastrointestinal tract), at least a portion of the containing structure degrades such that the resident structure obtains a configuration configured for gastric residence.

The phrase "location internal to a subject" as used herein generally refers to an internal cavity (e.g., the mouth, the esophagus, the small intestine, the colon, the duodenum, the ileum, the jejunum, the stomach, or the rectum) of the subject. In some embodiments, the location internal to the subject is proximate (e.g., adjacent, directly adjacent) a gastric orifice such as the pylorus. In some embodiments, the resident structure is configured to reside adjacent the gastric orifice such as the pylorus (e.g., the resident structure has a largest cross-sectional area which does not permit passage through the pylorus). Those of ordinary skill in the art would understand, based upon the teachings of this specification, that a resident structure is retained at a location internal to a subject when it does not substantially transit from said location absent a physical, chemical, or mechanical change to the resident structure. By way of example and without wishing to be bound by a literal interpretation of such, a resident structure is retained a location internal to a subject when it remains substantially proximate (e.g., adjacent, in contact with) that location over the duration of a residence time period (e.g., greater than or equal to 24 hours). By contrast, by way of a comparative example and without wishing to be bound by a literal interpretation of such, a resident structure is not considered retained at a location internal to a subject as it transits the gastrointestinal tract (e.g., driven by gastrointestinal forces and/or motion such that it moves through the gastrointestinal tract). For example, a device that remains internal to a subject but transits the gastrointestinal tract over e.g., greater than or equal to 24 hours is not intended to be a device that is retained at a location internal to a subject for said greater than or equal to 24 hours, despite being internal to the subject. By way of example, a resident structure that remains proximate the pylorus of the subject e.g., greater than or equal to 24 hours is intended to be considered a resident structure that is retained at the location internal to the subject for said greater than or equal to 24 hours. Other residence time periods are also possible and are described in more detail below.

Those of ordinary skill in the art would understand, based upon the teachings of this specification, that residence does not require a strict adherence to a geometrically defined relative to location internal to a subject such that the resident structure may move (e.g., as a result of gastrointestinal forces/motion) while being retained at the location internal to the subject. By way of example, and without wishing to be bound by a literal interpretation of such, a resident structure is said to be retained e.g., in the stomach of the subject as long as the structure remains in the stomach and does not exit the stomach (e.g., via the pylorus) during the desired residence time period. In some embodiments, the structures described herein comprise a component that undergoes a change (e.g., a mechanical change) such that the resident structure exits the location internal to the subject (e.g., passes through the pylorus).

According to some embodiments, at least a portion of the resident structure is configured to degrade, dissolve, and/or disassociate into one or more forms capable of passing through a gastrointestinal tract (e.g., after a desired period of time). In some embodiments, the arms and/or core of the resident structure may be selected such that each arm and/or the core dissolves, degrades, mechanically weakens, and/or mechanically separates from the electronic component after a particular residence time period (and/or upon triggering from the electronic component). The term residence time period generally refers to the length of time during which the resident structure described herein is resided at a location internally of a subject as measured from the time initially present in the location internally of the subject to the time at which the resident structure no longer resides at the location internally of the subject due to, for example, degradation, dissolution, and/or exit of at least a portion of the resident structure from the location internally of the subject. In an illustrative embodiment, the resident structure may be orally administered such that the resident structure resides at a location internally of the subject such as the small intestine and exits the small intestine (e.g., after degradation of at least a portion of the resident structure such as the arms and/or the core), where the residence time period is measured as the length of time between when the resident structure initially resides in the small intestine and when the resident structure exits the small intestine.

In some embodiments, the arms of the resident structure may comprise a degradable material. In some cases, the arms, the core, and/or a linker(s) may be configured to mediate disassembly of the resident structure after, for example, delivery of a pharmaceutical agent for the residence time period (e.g., after greater than or equal to 24 hours), and safe passage through the lower intestinal tract of the subject. Exit from a location such as the small intestine may be achieved through changes in the mechanical properties of each arm (e.g., via biodegradation) such that the ability to resist passage through the small intestine compromised.

The term "subject," as used herein, refers to an individual organism such as a human or an animal. In some embodiments, the subject is a mammal (e.g., a human, a non-human primate, or a non-human mammal), a vertebrate, a laboratory animal, a domesticated animal, an agricultural animal, or a companion animal. Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the resident structure. In some embodiments, the resident structure is administered orally, to a subject.

In some embodiments, the resident structure comprises an electronic component. In an exemplary set of embodiments, the resident structure comprising an electronic component is administered such that the resident structure enters the stomach of the subject and is retained in the stomach for a residence period (e.g., of greater than or equal to 24 hours). The electronic component may be configured to transmit a signal from the electronic component to a device external (e.g., extracorporeal) of the stomach and/or configured to receive a signal from a device external (e.g., extracorporeal) of the stomach. For example, in some embodiments, the electronic component may be configured to transmit and/or receive physiological conditions about the subject such as e.g., temperature (e.g., gastric internal temperature), pH, pressure, or other biophysical characteristics. For example, the electronic component may comprise (and/or be in electronic communication with) one or more sensors configured to determine one or more physiological conditions about the subject. In some embodiments, the electronic component comprises one or more sensors (e.g., a biomolecular sensor, a gas sensor, a temperature sensor, a pressure sensor, a motion sensor, an accelerometer, a pH sensor, a biochemical sensor), a wireless identification microchip, and/or an imaging system (e.g., a camera). In some embodiments, the electronic component is configured to generate and/or receive a signal (e.g., a wireless signal). In some embodiments, the signal triggers the electronic component to release a pharmaceutical agent from the resident structure. In some embodiments, the signal provides a physiological condition of the subject to the device external of the stomach. In some embodiments, the signal mediates the exit of the electronic component from the stomach through the pylorus, as described herein.

In some embodiments, the electronic component comprises one or more drug delivery modules. For example, in some embodiments, the electronic component may be configured to, upon residence at a location internal to the subject, detect one or more biophysical conditions and/or deliver one or more pharmaceutical agents at the location internal to the subject. In some embodiments, the electronic component is configured to deliver (e.g., release) one or more pharmaceutical agents in response to a physiological condition of the subject, a signal from a sensor on the electronic component, and/or a signal received from a device external the subject.

In some embodiments, at the end of the residence period, the electronic component and or the resident structure is configured to pass from the location internal to the subject (e.g., exits the stomach through the pylorus). For example, as illustrated in FIG. 1A, resident structure 100 comprises an electronic component 110 linked to a second component 130 and two or more arms 120. In some embodiments, resident structure 100 has a first configuration 100A (e.g., a compressed configuration). In some embodiments, the first configuration is such that the resident structure may be administered to a subject (e.g., introduced orally) and will transit through the gastrointestinal tract until reaching a location internal to the subject (e.g., the stomach, proximate the pylorus). In some embodiments, resident structure 100 obtains a second configuration 100B (e.g., an expanded configuration) in which the resident structure is retained at the location internal to the subject and does not pass through any internal orifices (e.g., is retained in the stomach and does not pass into the pylorus) under normal physiological conditions. In configuration 100B, arms 120 and/or electronic component 110 expand such that resident structure 100 is retained. In some embodiments, resident structure 100 obtains a third configuration in which a degradable portion (e.g., component 130, arms 120) of the resident structure dissolves, degrades, mechanically weakens, and/or mechanically separates from the electronic component. In some such embodiments, the electronic component and/or the resident structure passes from the location internal to the subject (e.g., exits the stomach through the pylorus). As described herein, in some embodiments, resident structure 100 obtains configuration 100B for a desired residence time period.

For example, in some embodiments, the resident structure has a second configuration including a particular size and/or shape in a relaxed state (e.g., configuration 100B). In certain embodiments, the resident structure may be folded from the second configuration into a first, folded configuration (configuration 100A). For example, in some cases, the folded/compressed resident structure may be inserted within the capsule or other containment structure in the first configuration such that the resident structure can be administered (e.g., orally). The capsule or other containment structure can be, in some cases, configured to dissolve such that the resident structure is released at a particular location internal to the subject whereby upon release, it can reversibly revert to the second configuration (e.g., by elastic recoil). In some embodiments, the resident structure is configured to adopt a shape and/or size in vivo that slows or prevents further transit in a body (e.g., gastric, small intestine) cavity until a desired time (e.g., upon dissolution of the microneedles and/or the arms of the resident structure). In some embodiments, the resident structure adopts a shape and/or size configured for prolonged retention (e.g., gastric residence) upon release from a capsule/container and/or retaining structure/element. In some embodiments, the resident structure is configured for adopting a shape and/or size configured for gastric deployment (after being stored in its encapsulated/folded shape and/or size) for the residence time period. In some embodiments, the residence time period is greater than or equal to 24 hours, greater than or equal to 48 hours, greater than or equal to 3 days, at 7 days, greater than or equal to 1 month, greater than or equal to 6 months, or greater than or equal to 1 year. In certain embodiments, the residence time period is less than or equal to 2 years, less than or equal to 1 year, less than or equal to 6 months, less than or equal to 1 month, less than or equal to 7 days, less than or equal to 3 days, or less than or equal to 48 hours. Combinations of the above-referenced ranges are also possible (e.g., greater than or equal to 24 hours and less than or equal to 2 years, greater than or equal to 24 hours and less than or equal to 1 year, greater than or equal to 48 hours and less than or equal to 7 days, greater than or equal to 3 days and less than or equal to 1 month, greater than or equal to 7 days and less than or equal to 6 months, greater than or equal to 1 month and less than or equal to 1 year). Other ranges are also possible.

In some embodiments, the resident structure is configured and designed such that a pharmaceutical agent is released from the resident for at least a portion of the residence time period, in one or more of the ranges listed above (e.g., greater than or equal to 24 hours and less than or equal to 2 years).

Figure 1B:
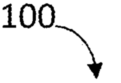
FIG. 1B is a schematic illustration of a gastric resident structure, according to one set of embodiments.
Figure 1B:
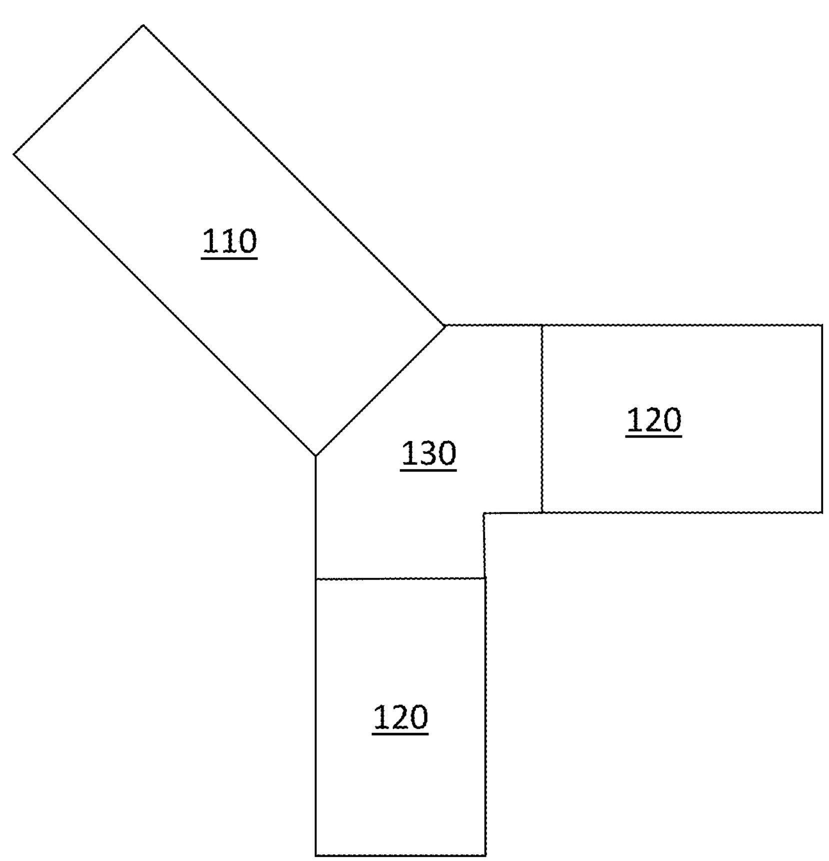

Referring now to FIG. 1B, in some embodiments, a resident structure 102 comprises an electronic component 110 associated with (e.g., connected to) a second component 130 and two or more arms 120. In some embodiments, second component 130 is an elastic component (e.g., an elastic core). Elastic components are described in more detail, below. In some embodiments, second component 130 and arms 120 comprise the same material. In certain embodiments, second component 130 and arms 120 comprise different materials. In an exemplary set of embodiments, second component 130 comprises a thermoplastic polyurethane and arms 120 comprise polylactic acid. Other materials are also possible and are described in more detail below.

In some embodiments, the resident structure comprises a degradable component linked to the electronic component such that the degradable component mediates the exit of the electronic component from the stomach through the pylorus of the subject. For example, in some embodiments, at least a portion of second component 130 is configured to dissolve, degrade, mechanically weaken, and/or mechanically separate from the electronic component such that the electronic component exits the location internal to the subject (e.g., passes from the stomach through the pylorus). In some embodiments, at least a portion of each arm 120 is configured to dissolve, degrade, mechanically weaken, and/or mechanically separate from the second component such that the electronic component exits the location internal to the subject (e.g., passes from the stomach through the pylorus).

Figure 1C:
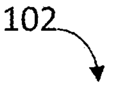
FIG. 1C is a schematic illustration of a gastric resident structure, according to one set of embodiments.
Figure 1C:
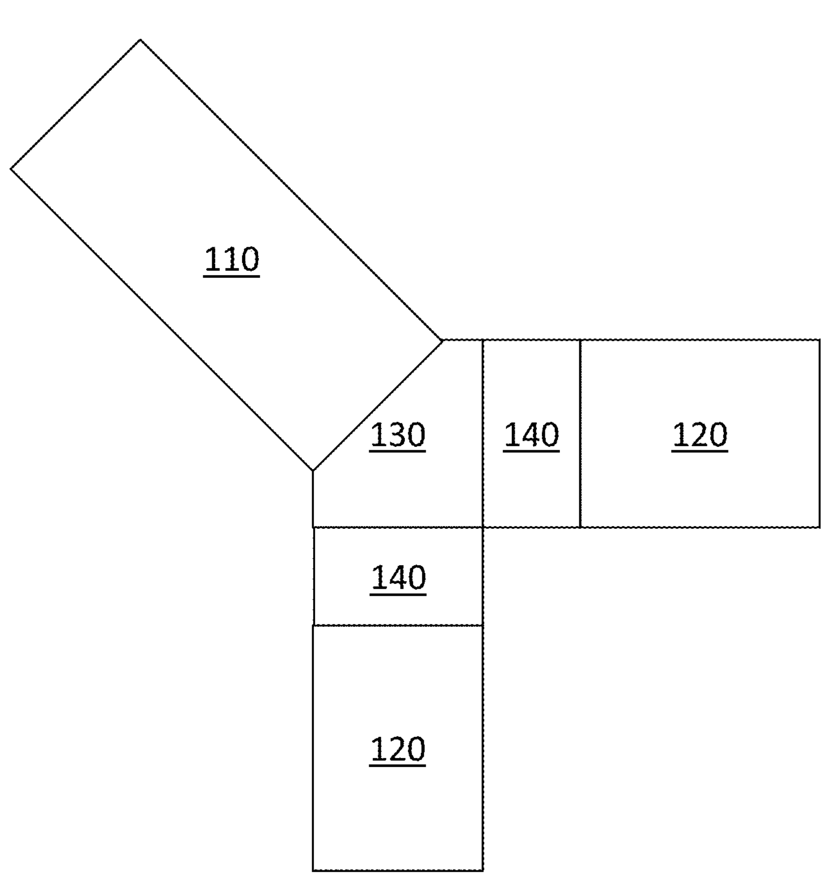

In some embodiments, a signal (e.g., from the electronic component, from an external device received by the electronic component) triggers the degradable component(s) to dissolve, degrade, mechanically weaken, and/or mechanically separate from the electronic component. In some embodiments, as shown illustratively in FIG. 1C, a resident structure 104 comprises electronic component 110, two or more arms 120, a second component 130 (e.g., an elastic component), and linkers 140. In some embodiments, linkers 140 are degradable linkers configured to dissolve, degrade, mechanically weaken, and/or mechanically separate from the electronic component such that the electronic component exits the location internal to the subject (e.g., passes from the stomach through the pylorus). While two linkers 140 are shown in FIG. 1C, those of ordinary skill in the art would understand that additional (or fewer) linkers are possible and may be positioned at other locations in the resident structure (e.g., such that when the linker(s) dissolve, degrade, mechanically weaken, and/or mechanically separate the electronic component exits the location internal to the subject).

For example, in some embodiments, the electronic component is delivered to a subject by administering orally, to a subject, a resident structure comprising an electronic component such that the electronic component is retained at a location internal to the subject for at least about 24 hours, wherein the resident structure comprises an elastic core (e.g., the second component), two or more polymeric arms associated with the elastic core, and the electronic component associated with the elastic core.

In some embodiments, the electronic component is removed from the location internal to the subject by degrading the degradable linker(s) and/or one or more additional degradable components.

In some embodiments, the degradable component(s) (or arms) may be dissolved, degraded, mechanically weaken, and/or mechanically separated from the electronic component by applying a voltage to the degradable component. In some embodiments, the electronic component is configured to apply the voltage to the degradable component(s), as described in more detail below.

In some embodiments, the degradable component(s) comprise a plurality of carbonaceous particles, carbon nanotubes, and/or conductive particles e.g., such that when the voltage is applied, the degradable component dissolves, degrades, mechanically weakens, and/or mechanically separates. Without wishing to be bound by theory, the plurality of carbonaceous particles, carbon nanotubes, and/or conductive particles may generate heat in the presence of an applied voltage such that the degradable component(s) mechanically weaken (e.g., undergo thermoplastic weakening). In some embodiments, the degradable component comprises an electroactive adhesive (e.g., a mixture of a low melting temperature polymer with electrically conductive nanomaterials). In an exemplary embodiment, the electroactive adhesive comprises poly(caprolactone) and a plurality of carbon nanotubes. In some embodiments, the degradable components comprise a plurality of particles comprising graphene and/or nickel. The carbonaceous/conductive particles may have any suitable average cross-sectional dimension (e.g., diameter). In some embodiments, the degradable component(s) comprise a plurality of particles (e.g., carbonaceous particles, conductive particles) having an average cross-sectional dimension of greater than or equal to 0.1 microns, greater than or equal to 0.2 microns, greater than or equal to 0.5 microns, greater than or equal to 1 micron, greater than or equal to 2 microns, greater than or equal to 5 microns, greater than or equal to 10 microns, greater than or equal to 20 microns, greater than or equal to 50 microns, greater than or equal to 100 microns, greater than or equal to 200 microns, greater than or equal to 500 microns, or greater than or equal to 750 microns. In some embodiments, the average cross-sectional dimension is less than or equal to 1000 microns, less than or equal to 750 microns, less than or equal to 500 microns, less than or equal to 200 microns, less than or equal to 50 microns, less than or equal to 20 microns, less than or equal to 10 microns, less than or equal to 5 microns, less than or equal to 2 microns, less than or equal to 1 microns, less than or equal to 0.5 microns, or less than or equal to 0.2 microns. Combinations of the above-referenced ranges are possible (e.g., greater than or equal to 0.1 microns and less than or equal to 1000 microns). Other ranges are also possible.

As used herein, the term "nanotube" is given its ordinary meaning in the art and refers to a substantially cylindrical molecule or nanostructure comprising a fused network of primarily six-membered aromatic rings. In some cases, nanotubes may resemble a sheet of graphite formed into a seamless cylindrical structure. It should be understood that the nanotube may also comprise rings or lattice structures other than six-membered rings. Nanotubes may have a diameter of the order of nanometers and a length on the order of millimeters, or, on the order of tenths of microns, resulting in an aspect ratio greater than 100, 1000, 10,000, or greater. In some cases, the nanotube is a carbon nanotube (CNT). The term "carbon nanotube" refers to nanotubes comprising primarily carbon atoms and includes single-walled nanotubes (SWNTs), double-walled nanotubes (DWNTs), multi-walled nanotubes (MWNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube). In some cases, the nanotube may have a diameter less than 1 μm, less than 100 nm, 50 nm, less than 25 nm, less than 10 nm, or, in some cases, less than 1 nm (or greater than or equal to nm, greater than or equal to 1 nm, greater than or equal to 10 nm, greater than or equal to 25 nm, greater than or equal to 50 nm, or greater than or equal to 100 nm). Combinations of the above-referenced ranges are also possible (e.g., less than 1 micron and greater than or equal to 0.5 nm). Other ranges are also possible.

As described above, in some embodiments, the resident structure has a particular configuration including a particular size and/or shape (e.g., a multi-armed star) in a relaxed state. In certain embodiments, the resident structure may be folded such that it obtains a second, compressed configuration. For example, in some cases, the resident structure may be folded within a capsule in the second configuration such that the resident structure may be delivered orally. The capsule may, in some cases, dissolve such that the resident structure is released at a particular location internal to the subject (e.g., in the stomach) and reversibly obtain the first configuration (i.e. recoil). In some embodiments, the device is configured to adopt a shape and/or size that slows or prevents further transit in a gastric cavity (e.g., passage from the body of the stomach through the pylorus). In some embodiments, the device adopts a shape and/or size capable of retention (e.g., gastric residence) upon release from the soluble container and/or soluble retaining element. In some embodiments, the device is capable of adopting a shape and/or size capable of gastric residence after being stored in its encapsulated shape and/or size for durations greater than 24 hours, including up to about one year. In some embodiments, the mechanical properties of the device are optimized for safe transient retention in an internal orifice such as the gastric cavity for durations greater than 24 hours, including up to about one year.

Certain of the devices, systems, and methods described herein can be useful, for example, in achieving gastric residence and/or slowed transit via oral administration for extended in vivo residence and administration of therapeutic, diagnostic, and/or enhancement agents. The devices and systems described herein may offer several advantages as compared to traditional residence and/or orally administered devices and systems including, for example, the ability to adopt a shape and/or size small enough to be ingested by a subject; adopt a shape and/or size that slows or prevents further transit in the gastric cavity (e.g., passage from the body of the stomach through the pylorus); load high levels (e.g., high mass) of therapeutic, diagnostic, and/or enhancement agents; control release of therapeutic, diagnostic, and/or enhancement agents with low to no potential for burst release; maintain stability of therapeutic, diagnostic, and/or enhancement agents in a hostile environment such as the gastric environment for an extended duration; maintain safety with low to no potential for gastric or intestinal obstruction and/or perforation; and/or degrade/dissolve/dissociate into one or more forms capable of passing through a gastrointestinal tract. In certain embodiments, the devices and systems described herein can be configured with durable residence times greater than at least twenty-four hours and lasting up to about one year, or more. In some embodiments, the systems, devices, and methods described herein are compatible with subjects, including, but not limited to humans and non-human animals. In further embodiments, the systems and devices can be configured to deliver a wide variety of therapeutic, diagnostic, and/or enhancement agents, thus potentially increasing and even maximizing adherence rates.

Those of ordinary skill in the art would be capable of selecting suitable methods for forming the electronic component, arm(s), and/or elastic core, based upon the teachings of this specification. In an exemplary set of embodiments, at least a portion of the resident structure (e.g., at least a portion of the electronic component, arm(s), and/or elastic core) are formed using 3D printing.

In some embodiments, the electronic component comprises wireless capabilities for enabling suitable communication with other devices/systems (e.g., for controlling aspects of the electronic component, controlling/monitoring physiological conditions of the subject (e.g., at the location internal to the subject), etc.). Wireless devices are generally known in the art and may include, in some cases, LTE, WiFi and/or Bluetooth systems. In some embodiments, the electronic components described herein comprise such a wireless device.

In some embodiments, the electronic component may be configured to adjust various parameters based on physiological and/or external metrics. For example, in some embodiments, the electronic component is configured to adjust the rate and/or amount of a pharmaceutical agent released from the electronic component (e.g., stored within one or more reservoirs associated with the electronic component) e.g., in response to a signal from a sensor in electrical or wireless communication with and/or associated with (e.g., embedded within) the electronic component. In some embodiments, the electronic component adjusts the rate and/or amount of a pharmaceutical agent released from the electronic component in response to an input from the user and/or a signal from the sensor. In some embodiments, the electronic component is associated with one or more reservoirs configured for the release of a pharmaceutical agent. In some embodiments, the one or more reservoirs may release a portion of the pharmaceutical agent contained therein in response to a signal received from a sensor in electrical or wireless communication with the electronic component.

Non-limiting examples of suitable sensors for use with the structures and methods described herein include temperature sensors (e.g., monitoring internal temperature, ambient temperature, temperature of a component associated with the electronic component such as a thermally sensitive polymer), physiological/biometric sensors (e.g., heart rate, electrical activity, neuronal activity), accelerometers (e.g., for measuring breathing rate, activity levels, sleeping behavior/patterns), and environmental sensors (e.g., pH, biologic concentration, chemical concentration).

In some embodiments, the electronic component is associated with and/or comprises a power source. The power source may include any appropriate material(s), such as one or more batteries, photovoltaic cells, etc. Non-limiting examples of suitable batteries include Li-polymer (e.g., with between 100 and 1000 mAh of battery life), Li-ion, nickel cadmium, nickel metal hydride, silver oxide, or the like. In some cases, the battery may apply a voltage (e.g., to a degradable material as described herein) in response to a physiological and/or external metric and/or signal (e.g., by a user). For example, the voltage may be used to trigger the exit of the resident structure by e.g., applying a voltage to thermally sensitive degradable component as described herein. For example, the average magnitude of the voltage applied to the degradable component(s) may be between 0.001 to 0.01 V, between 0.01 to 0.1 V, between 0.1 V and 10.0 V, between 1.0 V and 8.0 V, between 2.0 V and 5.0 V, between 0.1 V and 5.0 V, between 0.1 V and 1.5 V, between 0.1 V and 1.0 V, between 1.0 V and 3.0 V, between 3.0 V and 8.0 V, or any other appropriate range.

Any electronic component circuitry may be implemented by any suitable type of analog and/or digital circuitry. For example, the electronic component circuitry may be implemented using hardware or a combination of hardware and software. When implemented using software, suitable software code can be executed on any suitable processor (e.g., a microprocessor) or collection of processors. The one or more electronic components can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein may, in some cases, comprise at least one computer-readable storage medium (e.g., RAM, ROM, EEPROM, flash memory or other memory technology, or other tangible, non-transitory computer-readable storage medium) encoded with a computer program (i.e., a plurality of executable instructions) that, when executed on one or more processors, performs the above-discussed functions of one or more embodiments. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

In some embodiments, the second component (e.g., the elastic core) is an elastic polymeric component. In certain embodiments, the use of an elastic polymeric component and may impart particular mechanical properties to the structure. For example, in some cases, the structure may be capable of undergoing relatively high compressive forces (e.g., compressive forces present within the stomach and/or intestine of a subject) such that the structure does not break and/or is retained at a location internally of the subject (e.g., at or above an orifice such as the pylorus). In certain embodiments, the structure may be capable of being folded (e.g., without breaking). For example, the elastic polymeric component may be capable of undergoing relatively high levels of bending stresses without breaking and/or being permanently significantly deformed. In some embodiments, the elastic polymeric component and/or the structure may be capable of substantial recoil. That is to say, after mechanically deforming the elastic polymeric component and/or the structure comprising the elastic polymeric component, the structure may return substantially to its original configuration prior to the mechanical deformation being applied (e.g., having substantially minimal creep deformation).

Several screening tests may be used to determine suitable materials for use as the elastic polymeric component. For example, the elastic polymeric component may be capable of undergoing at least about 45 degrees, at least about 60 degrees, at least about degrees, at least about 120 degrees, at least about 150 degrees, or about 180 degrees of mechanical bending deformation without breaking. In certain embodiments, the elastic polymeric component may be capable of undergoing less than or equal to about 180 degrees, less than or equal to about 150 degrees, less than or equal to about 120 degrees, less than or equal to about 90 degrees, or less than or equal to about 60 degrees of mechanical bending deformation without breaking. Combinations of the above-referenced ranges are also possible (e.g., between about 45 degrees and about 180 degrees, between about 60 degrees and about 180 degrees, between about 60 degrees and about 120 degrees, between about 90 degrees and about 180 degrees). Other ranges are also possible.

In some cases, the elastic polymeric component may be capable of remaining in a deformed configuration (e.g., at least about 45 degrees of mechanical bending deformation) for a relatively prolonged period of time. For example, in some embodiments, the elastic polymer component has a shelf-life in a deformed configuration (e.g., at least about 45 degrees of mechanical bending deformation) of at least about 24 hours, at least about 1 week, at least about 1 month, at least about 1 year, or at least about 2 years and be capable of returning (i.e. recoiling) substantially to its pre-deformation configuration. In certain embodiments, the elastic polymer component has a shelf life in a deformed configuration of less than or equal to about 3 years, less than or equal to about 2 years, less than or equal to about 1 year, less than or equal to about 1 month, or less than or equal to about 1 week and be capable of returning (i.e. recoiling) substantially to its pre-deformation configuration. Combinations of the above-referenced ranged are also possible (e.g., between about 24 hours and about 3 years, between about 1 week and 1 year, between about 1 year and 3 years). Other ranges are also possible.

In some embodiments, the elastic polymeric component is relatively flexible. In certain embodiments, the elastic polymeric component may be selected such that it is capable of undergoing large angle deformation for relatively long periods of time without undergoing significant non-elastic deformation. In some such embodiments, the elastic polymeric component may have a strength of recoil sufficient to substantially return the elastic polymeric component to its pre-deformed shape within less than about minutes, within less than about 10 minutes, within less than about 5 minutes, or within less than about 1 minute after release of the mechanical deformation. Those skilled in the art would understand that returning to its pre-deformed shape shall be understood to not require absolute conformance to a mathematical definition of shape, but, rather, shall be understood to indicate conformance to the mathematical definition of shape to the extent possible for the subject matter so characterized as would be understood by one skilled in the art most closely related to such subject matter.

In some embodiments, the elastic polymeric component has a particular elastic modulus. In some embodiments, the elastic modulus of the elastic polymeric component ranges between about 0.1 MPa and about 30 MPa. In some embodiments, the elastic modulus of the elastic polymeric component is at least about 0.1 MPa, at least about 0.2 MPa, at least about 0.3 MPa, at least about 0.5 MPa, at least about 1 MPa, at least about 2 MPa, at least about 5 MPa, at least about 10 MPa, at least about 20 MPa, or at least about 25 MPa. In certain embodiments, the elastic modulus of the elastic polymeric component is less than or equal to about 30 MPa, less than or equal to about 25 MPa, less than or equal to about 20 MPa, less than or equal to about 10 MPa, less than or equal to about 5 MPa, less than or equal to about 2 MPa, less than or equal to about 1 MPa, less than or equal to about 0.5 MPa, less than or equal to about 0.3 MPa, or less than or equal to about 0.2 MPa. Combinations of the above referenced ranges are also possible (e.g., between about 0.1 MPa and about 30 MPa, between about 0.3 MPa and about 10 MPa). Other ranges are also possible. Those skilled in the art would be capable of selecting suitable methods for determining the elastic modulus of a polymeric component including, for example, tensile mechanical characterization under ASTM D638 and/or compressive mechanical characterization under ASTM D575.

In some embodiments, the elastic polymeric component undergoes a relatively low amount of creep during mechanical deformation. For example, in certain embodiments, the elastic polymeric component has a minimum creep rate of less than or equal to about 0.3 mm/mm/hr, less than or equal to about 0.2 mm/mm/hr, less than or equal to about 0.1 mm/mm/hr, less than or equal to about 0.08 mm/mm/hr, less than or equal to about 0.05 mm/mm/hr, less than or equal to about 0.03 mm/mm/hr, or less than or equal to about 0.02 mm/mm/hr. In certain embodiments, the elastic polymeric component has a minimum creep rate of at least about 0.01 mm/mm/hr, at least about mm/mm/hr, at least about 0.03 mm/mm/hr, at least about 0.05 mm/mm/hr, at least about 0.08 mm/mm/hr, at least about 0.1 mm/mm/hr, or at least about 0.2 mm/mm/hr. Combinations of the above referenced ranges are also possible (e.g., between about 0.01 mm/mm/hr and about 0.3 mm/mm/hr, between about 0.02 mm/mm/hr and about 0.1 mm/mm/hr, between about 0.02 mm/mm/hr and about 0.05 mm/mm/hr, between about mm/mm/hr and about 0.3 mm/mm/hr). Other ranges are also possible. Minimum creep rate can be determined, in some embodiments, according to ASTM D-638. Briefly, a sheet of the elastic polymeric material is prepared, as described below, and cut into a standard dumbbell die. The specimens can be loaded into grips of an Instron testing machine and the gauge length measured using a digital micrometer. A constant stress corresponding to 30% of the ultimate tensile strength of each material may be applied to the specimens for 60 min at constant temperature (e.g., room temperature) and the creep (in mm/mm) versus time (in hours) can be plotted. The minimum creep rate is the slope of the creep vs. time curve prior to secondary creep.

Those skilled in the art would be capable of determining suitable methods for tuning the mechanical properties (e.g., elastic modulus, creep behavior) of the elastic polymeric component by, for example, varying the molar ratios of monomeric and/or polymeric units (e.g., increasing the amount of high molecular weight polycaprolactone or other polymers used in the elastic polymeric component), varying polymer cross-linking density, varying the concentration of cross-linking agents used in the formation of the polymer, varying the crystallinity of the polymer (e.g., by varying the ratio of crystalline and amorphous regions in the polymer) and/or the use of additional or alternative materials (e.g., incorporating materials such as bis(isocyanatomethyl)-cyclohexane).

In some embodiments, the elastic polymeric component does not substantially swell in the presence of biological fluids such as blood, water, bile, gastric fluids, and/or the like. In some embodiments, the elastic polymer component swells between about 0.01 vol % and about 10 vol % in a biological fluid as compared to the volume of the elastic polymer component in the dry state (e.g., at atmospheric conditions and room temperature). For example, in certain embodiments, the elastic polymeric component swells by less than about 10 vol %, less than about 5 vol %, less than about 2 vol %, or less than about 1 vol % in a biological fluid as compared to the volume of the elastic polymeric component in the dry state (e.g., at atmospheric conditions and room temperature). Those skilled in the art would be capable of selecting suitable methods for determining the amount of swelling of an elastic polymeric component based upon the teachings of this specification including, for example, measuring the volume of the elastic polymeric component in the dry state at atmospheric conditions and room temperature, submerging the component in a biological fluid (e.g., blood, water, bile, gastric fluids, and/or the like) and measuring the percent change in volume of the component after about 60 minutes.

The elastic polymeric component is generally biocompatible. The term "biocompatible," as used herein, refers to a polymer that does not invoke an adverse reaction (e.g., immune response) from an organism (e.g., a mammal), a tissue culture or a collection of cells, or if the adverse reaction does not exceed an acceptable level. In some embodiments, the elastic polymeric component comprises polymers, their networks, and/or multi-block combinations of, for example, polyesters, including but not limited to, polycaprolactone, poly(propylene fumarate), poly(glycerol sebacate), poly(lactide), poly(glycol acid), poly(lactic-glycolic acid), polybutyrate, and polyhydroxyalkanoate; polyethers, including but not limited to, poly(ethylene oxide) and poly(propylene oxide); polysiloxanes, including but not limited to, poly(dimethylsiloxane); polyamides, including but not limited to, poly(caprolactam); polyolefins, including but not limited to, polyethylene; polycarbonates, including but not limited to poly(propylene oxide); polyketals; polyvinyl alcohols; polyoxetanes; polyacrylates/methacrylates, including but not limited to, poly(methyl methacrylate) and poly(ethyl-vinyl acetate); polyanhydrides; and polyurethanes (e.g., thermoplastic polyurethanes). In some embodiments, the polymer is cross-linked. In some embodiments, the elastic polymeric component comprises a polymer composite comprising two or more chemically similar polymers or two or more chemically distinct polymers. In an exemplary embodiment, the elastic polymeric component comprises an isocyanate cross-linked polyurethane generated from low molecular weight monomers such as polycaprolactone. In some embodiments, the low molecular weight monomers comprise one or more hydroxyl functional groups (e.g., a diol, a triol).

In some embodiments, each arm has particular mechanical properties such that the arm material resists brittle breakage but is sufficiently stiff such that it may withstand internal physiological pressure and/or maintain residence of the structure. In some embodiments, the arm(s) comprises polymers, their networks, and/or multi-block combinations of, for example, polyesters, including but not limited to, polycaprolactone, poly(propylene fumarate), poly(glycerol sebacate), poly(lactide), poly(glycol acid), poly(lactic-glycolic acid), polybutyrate, and polyhydroxyalkanoate; polyethers, including but not limited to, poly(ethylene oxide) and poly(propylene oxide); polysiloxanes, including but not limited to, poly(dimethylsiloxane); polyamides, including but not limited to, poly(caprolactam); polyolefins, including but not limited to, polyethylene; polycarbonates, including but not limited to poly(propylene oxide); polyketals; polyvinyl alcohols; polyoxetanes; polyacrylates/methacrylates, including but not limited to, poly(methyl methacrylate) and poly(ethyl-vinyl acetate); polyanhydrides; and polyurethanes (e.g., thermoplastic polyurethanes). In some embodiments, the polymer is cross-linked. In some embodiments, the arm(s) comprises a polymer composite comprising two or more chemically similar polymers or two or more chemically distinct polymers. In an exemplary embodiment, the arm(s) comprises an isocyanate cross-linked polyurethane generated from low molecular weight monomers such as polycaprolactone. In some embodiments, the low molecular weight monomers comprise one or more hydroxyl functional groups (e.g., a diol, a triol).

Several screening tests may be used to select suitable materials for use as the arm(s). For example, the arm(s) may be selected such that the arm(s) has a flexural moduli greater than about 100 MPa, greater than about 120 MPa, greater than about 150 MPa, or greater than about 200 MPa. In some embodiments, the arm(s) has a flexural modulus less than or equal to about 250 MPa, less than or equal to about 200 MPa, less than or equal to about 150 MPa, or less than or equal to about 120 MPa. Combinations of the above referenced ranges are also possible (e.g., between about 100 MPa and about 250 MPa). Other ranges are also possible. Those skilled in the art would be capable of selecting suitable methods for determining the flexural moduli of a polymeric component including, for example, plotting the flexural stress versus strain and taking the slope of the linear portion of the curve.

In certain embodiments, the arm(s) may be selected to have a flexural strength of at least about 10 MPa. For example, in some embodiments, the arm(s) has a flexural strength of at least about 10 MPa, at least about 15 MPa, at least about 20 MPa, at least about 30 MPa, or at least about 40 MPa. In certain embodiments, the arm(s) has a flexural strength of less than or equal to about 50 MPa, less than or equal to about 40 MPa, less than or equal to about 30 MPa, less than or equal to about 20 MPa, or less than or equal to about 15 MPa. Combinations of the above referenced ranges are also possible (e.g., between about 10 MPa and about 50 MPa). Other ranges are also possible. Those skilled in the art would be capable of selecting suitable methods for determining the flexural strength of the arm(s) including, for example, determining the flexural stress at failure of the polymeric material.

The arm(s) materials may be selected such that they maintain their mechanical properties over a residence time period (e.g., during the release of the active substance and/or during residence in an orifice). Residence time periods are described in more detail, below. In some embodiments, the arm(s) materials are selected such that the device may be retained within an orifice located internally of the subject (e.g., a gastric orifice) for at least 24 hours, at least 48 hours, at least one week, at least one month, or at least one year. In certain embodiments, the arm(s) materials are selected such that the device may be retained within an orifice location internally of the subject for less than or equal to about 2 years, less than or equal to about 1 year, less than or equal to aboutl month, less than or equal to about 1 week, or less than or equal to about 48 hours. Combinations of the above-referenced ranges are also possible (e.g., between about 24 hours and about 2 years, between about 48 hours and about 2 years, between about 1 week and about 1 year). Other ranges are also possible.

As described above, in some embodiments, at least one of the two or more arms may be configured to dissolve, degrade, mechanically weaken, and/or mechanically separate from the electronic component such that the electronic component passes from the stomach through the pylorus after a desired residence time (and/or upon triggering from the electronic component).

In some embodiments, the electronic component, the second component, one or more arm(s), and/or the linker comprises an enteric polymer. In some embodiments, the enteric polymer includes, but is not limited to, cellulose acetate phthalate (CAP), hypromellose (INN) or hydroxypropyl methylcellulose (HPMC), and EUDRAGIT® (available from Evonik Industries AG (Essen, Germany)).

In some embodiments, the dissolution of an enteric polymer can be triggered by, for example, ingestion of an alkali solution. In some embodiments, the enteric polymer has the capacity for dissolution between pH 4-8. According to some embodiments, the enteric polymer is selected such that the enteric polymer is stable in an acidic gastric environment (i.e., having a pH1 to pH4) but dissolves in a more alkali region of the gastrointestinal tract distal to the pylorus (i.e., having a pH greater than 5.5) and can serve as a linker.

For example, in certain embodiments, the enteric polymer does not substantially degrade at a pH ranging between about 1 and about 5. In some embodiments, the enteric polymer does not substantially degrade at a pH of at least about 1, at least about 2, at least about 3, at least about 4, or at least about 4.5. In certain embodiments, the enteric polymer does not substantially degrade at a pH of less than or equal to about 5, less than or equal to about 4.5, less than or equal to about 4, less than or equal to about 3, or less than or equal to about 2. Combinations of the above reference ranges are also possible (e.g., between about 1 and about 4.5, between about 1 and about 5, between about 1 and 4). Other ranges are also possible.

In certain embodiments, the enteric polymer degrades substantially at a pH ranging between about 4 and about 8. In some embodiments, the enteric polymer degrades substantially at a pH of at least about 4, at least about 5, at least about 6, at least about 6.5, at least about 7, or at least about 7.5. In certain embodiments, the enteric polymer degrades substantially at a pH of less than or equal to about 8, less than or equal to about 7.5, less than or equal to about 7, less than or equal to about 6.5, less than or equal to about 6, or less than or equal to about 5. Accommodations of the above reference ranges are also possible (e.g., between about 4 and about 8, between about 5 and about 8, between about 6.5 and about 7.5). Other ranges are also possible.

Those skilled in the art would be capable of selecting suitable methods for determining degradation of the enteric polymers based upon the teachings of the specification including, determining the solubility of the enteric polymer in an aqueous solution having a pH of less than about 3 and/or dissolving the enteric polymer in aqueous solution having a pH of greater than or equal to about 6, measured at body temperature (e.g., between about 35° C. and about 38° C.) over time period of between about 4 and about 40 days.

In some embodiments, the enteric polymer is an enteric elastomer. In certain embodiments, the enteric elastomer exhibits reversible elongation when stretched from 50% to 1500% of its initial length. For example, in some embodiments, the enteric elastomer exhibits reversible elongation when stretched from at least about 50%, at least about 100%, at least about 200%, at least about 400%, at least about 500%, at least about 1000%, at least about 1200%, or at least about 1400% of its initial length. That is to say, in some embodiments, the enteric elastomer has difference in average length after deformation versus before deformation (e.g., stretching) of less than about 10%, less than about 5%, less than about 2%, or less than about 1%. In certain embodiment, the enteric elastomer exhibits reversible elongation when stretched from less than or equal to about 1500%, less than or equal to about 1400%, less than or equal to about 1200%, less than or equal to about 1000%, less than or equal to about 500%, less than or equal to about 400%, less than or equal to about 200%, or less than or equal to about 100% of its initial length. Combinations of the above referenced ranges are also possible (e.g., between about 50% and about 1500%, between about hundred percent and about 1500%, between about 200% and about 1000%, between about 500% and about 1400%). Other ranges are also possible.

In certain embodiments, the enteric elastomer has an elastic modulus ranging between about 0.1 MPa and about 100 MPa. In some embodiments, the elastic modulus of the enteric elastomer is at least about 0.1 MPa, at least about 0.2 MPa, at least about MPa, at least about 0.5 MPa, at least about 1 MPa, at least about 2 MPa, at least about 5 MPa, at least about 10 MPa, at least about 25 MPa, or at least about 50 MPa. In certain embodiments, the elastic modulus of the enteric elastomer is less than or equal to about 100 MPa, less than or equal to about 50 MPa, less than or equal to about 25 MPa, less than or equal to about 10 MPa, less than or equal to about 5 MPa, less than or equal to about 2 MPa, less than or equal to about 1 MPa, less than or equal to about 0.5 MPa, less than or equal to about 0.3 MPa, or less than or equal to about 0.2 MPa. Combinations of the above referenced ranges are also possible (e.g., between about 0.1 MPa and about 100 MPa, between about 0.3 MPa and about 10 MPa). Other ranges are also possible. Those skilled in the art would be capable of selecting suitable methods for determining the elastic modulus of an enteric elastomer including, for example, tensile mechanical characterization under ASTM D638 and/or compressive mechanical characterization under ASTM D575.

In certain embodiments, the enteric elastomer comprises varying ratios of poly(acryloyl-6-aminocaproic acid) and poly(methacrylic acid-co-ethyl acrylate). In some embodiments, the enteric elastomer is a polymer gel with water content no greater than 40%.

In some embodiments, the enteric elastomer comprises a polymer of a (meth)acryloylaminoalkylene acid monomer, or salts thereof. In certain embodiments, the (meth)acryloylaminoalkylene acid monomer is selected from the group consisting of acryloyl-5-aminopentanoic acid, acryloyl-6-aminocaproic acid, acryloyl-7-aminoheptanoic acid, acryloyl-8-aminooctanoic acid, acryloyl-9-aminonoanoic acid, acryloyl-10-aminodecanoic acid, acryloyl-11-aminoundecanoic acid, acryloyl-12-aminododecanoic acid, methacryloyl-5-aminopentanoic acid, methacryloyl-6-aminocaproic acid, methacryloyl-7-aminoheptanoic acid, methacryloyl-8-aminooctanoic acid, methacryloyl-9-aminononoanoic acid, methacryloyl-10-aminodecanoic acid, methacryloyl-11-aminoundecanoic acid, methacryloyl-12-aminododecanoic acid, salts thereof, and combinations thereof.

In certain embodiments, the enteric elastomer comprises a homopolymer of acryloyl-6-aminocaproic acid or salts thereof. In some embodiments, the enteric elastomer comprises a copolymer of acryloyl-6-aminocaproic acid or salts thereof. In certain embodiments, enteric elastomer comprises poly(methacrylic acid-co-ethyl acrylate) or salts thereof. In some cases, the poly(methacrylic acid-co-ethyl acrylate) has a molar ratio of methacrylic acid monomer units to ethylacrylate monomer units of about 1:1.

In some embodiments, the enteric elastomer is a blend. For example, in certain embodiments, the enteric elastomer comprises a first enteric polymer (e.g., poly(acryloyl-6-aminocaproic acid)) and a second enteric polymer (e.g., poly(methacrylic acid-co-ethyl acrylate)). In some such embodiments, the weight ratio of the first enteric polymer to the second enteric polymer ranges from about 1:0 to about 1:3 (e.g., between about 1:0 to about 1:3).

In some embodiments, the resident structure (e.g., the electronic component) is pre-loaded with an active substance such as a therapeutic, diagnostic, and/or enhancement agents. In other embodiments, the resident structure (e.g., the electronic component) is loaded with therapeutic, diagnostic, and/or enhancement agents after it is already retained at a location internally to a subject, such as a gastric cavity. In some embodiments, the resident structure (e.g., the electronic component) is configured to maintain stability of therapeutic, diagnostic, and/or enhancement agents in a hostile physiological environment (e.g., the gastric environment) for an extended duration. In further embodiments, the resident structure (e.g., the electronic component) is configured to control release of therapeutic, diagnostic, and/or enhancement agents. In some embodiments, the resident structure (e.g., the electronic component) is pre-loaded and/or loaded with a combination of active substances. For example, in certain embodiments, the resident structure (e.g., the electronic component) comprises one or more, two or more, three or more, or four or more active substances (e.g., in one or more, two or more, three or more, or four or more reservoirs associated with the electronic component).

Agents can include, but are not limited to, any synthetic or naturally-occurring biologically active compound or composition of matter which, when administered to a subject (i.e., a human or nonhuman animal), induces a desired pharmacologic, immunogenic, and/or physiologic effect by local and/or systemic action. For example, the present disclosure is compatible with compounds or chemicals traditionally regarded as drugs, vaccines, and biopharmaceuticals, including molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., statins like rosuvastatin, nonsteroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, antiviral agents like entecavir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In some embodiments, the active substance is a radiopaque material such as tungsten carbide or barium sulfate.

In certain embodiments, the active substance is a therapeutic agent. As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Therapeutic agents include, without limitation, agents listed in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005. In some embodiments, the therapeutic agent may be selected from "Approved Drug Products with Therapeutic Equivalence and Evaluations," published by the United States Food and Drug Administration (F.D.A.) (the "Orange Book"). In some cases, the therapeutic agent is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention. In certain embodiments, the therapeutic agent is a small molecule. Exemplary classes of agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents (e.g., taxanes, such as paclitaxel and docetaxel; cisplatin, doxorubicin, methotrexate, etc.), antihistamines, antimigraine drugs, hormones, prostaglandins, antimicrobials (including antibiotics, antifungals, antivirals, antiparasitics), antimuscarinics, anxioltyics, bacteriostatics, immunosuppressant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated. These may be vitamins, supplements such as calcium or biotin, or natural ingredients such as plant extracts or phytohormones.

In some embodiments, the therapeutic agent is one or more antimalarial drugs. Exemplary antimalarial drugs include quinine, lumefantrine, chloroquine, amodiaquine, pyrimethamine, proguanil, chlorproguanil-dapsone, sulfonamides such as sulfadoxine and sulfamethoxypyridazine, mefloquine, atovaquone, primaquine, halofantrine, doxycycline, clindamycin, artemisinin and artemisinin derivatives. In some embodiments, the antimalarial drug is artemisinin or a derivative thereof. Exemplary artemisinin derivatives include artemether, dihydroartemisinin, arteether and artesunate. In certain embodiments, the artemisinin derivative is artesunate.

In another embodiment, the therapeutic agent is an immunosuppressive agent. Exemplary immunosuppressive agents include glucocorticoids, cytostatics (such as alkylating agents, antimetabolites, and cytotoxic antibodies), antibodies (such as those directed against T-cell recepotors or Il-2 receptors), drugs acting on immunophilins (such as cyclosporine, tacrolimus, and sirolimus) and other drugs (such as interferons, opioids, TNF binding proteins, mycophenolate, and other small molecules such as fingolimod).

In a further embodiment, the active substance is used to prevent restenosis in a drug-eluting stent. Exemplary agents include sirolimus (rapamycin), everolimus, zotarolimus, biolimus A9, cyclosporine, tranilast, paclitaxel and docetaxel.

In a further embodiment, the active substance is an antimicrobial agent. Exemplary antimicrobials include antibiotics such as aminoglycosides, cephalosporins, chloramphenicol, clindamycin, erythromycins, fluoroquinolones, macrolides including fidaxomicin and rifamycins such as rifaximin, azolides, metronidazole, penicillins, tetracyclines, trimethoprim-sulfamethoxazole, oxazolidinone such as linezolid, and glycopeptides such as vancomycin. Other antimicrobial agents include antifungals such as antifungal polyenes such as nystatin, amphotericin, candicidin and natamycin, antifungal azoles, allylamine antifungals and echinocandins such as micafungin, caspofungin and anidulafungin.

In some embodiments, the therapeutic agent is a small molecule drug having molecular weight less than about 2500 Daltons, less than about 2000 Daltons, less than about 1500 Daltons, less than about 1000 Daltons, less than about 750 Daltons, less than about 500 Daltons, less or than about 400 Daltons. In some cases, the therapeutic agent is a small molecule drug having molecular weight between 200 Daltons and 400 Daltons, between 400 Daltons and 1000 Daltons, or between 500 Daltons and 2500 Daltons.

In some embodiments, between 0.05 vol % to 99 vol % of the active substance is released between 24 hours and 1 year. In some embodiments, between about 0.05 vol % and about 99.0 vol % of the active substance is released from the electronic component (and/or one or more reservoirs associated with the electronic component) after a certain amount of time. In some embodiments, at least about 0.05 vol %, at least about 0.1 vol %, at least about 0.5 vol %, at least about 1 vol %, at least about 5 vol %, at least about 10 vol %, at least about 20 vol %, at least about 50 vol %, at least about 75 vol %, at least about 90 vol %, at least about 95 vol %, or at least about 98 vol % of the active substance associated with the electronic component (and/or one or more reservoirs associated with the electronic component) is released from the component after about after about 24 hours, after about 32 hours, after about 72 hours, after about 96 hours, or after about 192 hours. In certain embodiments, at least about 0.05 vol %, at least about 0.1 vol %, at least about 0.5 vol %, at least about 1 vol %, at least about 5 vol %, at least about 10 vol %, at least about 20 vol %, at least about 50 vol %, at least about 75 vol %, at least about 90 vol %, at least about 95 vol %, or at least about 98 vol % of the active substance associated with the polymeric component is released from the component after about 1 day, after about 5 days, after about 30 days, after about 60 days, after about 120 days, or after about 365 days. For example, in some cases, at least about 90 vol % of the active substance associated with the electronic component is released from the component after about 120 days.

In some embodiments, the active substance is released from the electronic component (and/or one or more reservoirs associated with the electronic component) at a particular initial average rate as determined by the first 24 hours of release (e.g., release of the active substance at the desired location internally of the subject, such as an internal orifice). In certain embodiments, the active substance is released at an average rate of at least about 1%, at least about 2%, at least about 5%, least about 10%, at least about 20%, at least about 30%, least about 50%, at least about 75%, at least about 80%, at least about 90%, at least about 95%, or at least about 98% of the initial average rate over a 24 hour period after the first 24 hours of release. In some embodiments, the active substance is released at an average rate of less than or equal to about 99%, less than or equal to about 98%, less than or equal to about 95%, less than or equal to about 90%, less than or equal to about 80%, less than or equal to about 75%, less than or equal to about 50%, less than or equal to about %, less than or equal to about 30%, less than or equal to about 20%, less than or equal to about 10%, less than or equal to about 5%, or less than or equal to about 2% of the initial average rate over a 24 hour period after the first 24 hours of release. Combinations of the above referenced ranges are also possible (e.g., between about 1% and about 99%, between about 1% and about 98%, between about 2% and about 95%, between about 10% and about 30%, between about 20% and about 50%, between about 30% and about 80%, between about 50% and about 99%). Other ranges are also possible.

The active substance may be released at an average rate over a 24 hour period of between about 1% and about 99% of the initial average release rate (measured during the first 24 hour period of release) between 48 hours and about 1 year (e.g., between 48 hours and 1 week, between 3 days and 1 month, between 1 week and 1 month, between 1 month and 6 months, between 3 months and 1 year, between 6 months and 2 years) after the initial release.

For example, in some cases, the active substance may be released at a rate of between about 1% and about 99% of the initial rate on the second day of release, the third day of release, the fourth day of release, the fifth day of release, the sixth day of release, and/or the seventh day of release.

In certain embodiments, the active substance may be released as a pulse release. For example, in some embodiments, the active substance may be released on the first day of release and another 24 hour period such as starting during the third day, the fourth day, or the fifth day, but not released on the alternative days. Those skilled in the art would understand that other days and/or combinations of pulsing and release are also possible. In some embodiments, the active substance is released in a burst release.

The active substance may be released at a relatively constant average rate (e.g., a substantially zero-order average release rate) over a time period of at least about 24 hours. In certain embodiments, the active substance is released at a first-order release rate (e.g., the rate of release of the active substance is generally proportional to the concentration of the active substance) of a time period of at least about 24 hours.

In some embodiments, at least a portion of the active substance loaded into the device is released continuously (e.g., at varying rates) over the residence time period. Residence time periods are described in more detail, below.

As described above, in some embodiments, the electronic component, arm(s), and/or second component (e.g., elastic core) are coupled. Those skilled in the art would understand that the term coupled generally refers to a physical linkage connecting two or more components. In some embodiments, the electronic component and second component may be coupled via an adhesive, by chemical interactions, and/or by interpenetrating (e.g., entangled) polymer chains. For example, in some embodiments, at least a portion of the electronic component and at least a portion of the second polymeric component are coupled via a bond such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus-nitrogen, carbon-nitrogen, metal-oxygen, or other covalent bonds. The hydrogen bond may be, for example, between hydroxyl, amine, carboxyl, thiol, and/or similar functional groups.

In certain embodiments, the electronic component and the second component are coupled via an adhesive (e.g., a biocompatible adhesive). Non-limiting examples of suitable adhesives include biocompatible polyurethanes and electroactive adhesives.

According to some embodiments, the resident structure is configured to degrade, dissolve, and/or disassociate into one or more forms capable of passing through a gastrointestinal tract. In some embodiments, the resident structure comprises one or more linkers designed for controlled and/or tunable degradation. According to some embodiments, one or more linkers are attached to and/or incorporated into the resident structure to separate out in a modular fashion the function of delivering therapeutic, diagnostic, and/or enhancement agents from controlling (e.g., triggering) and/or tuning degradation.

In certain embodiments, the second component (e.g., elastic core) and one or more arms are coupled together via a linker.

The resident structure may comprise one or more, two or more, or three or more types of linkers. For example, in an illustrative embodiment, the resident structure comprises a first linker capable of degradation at a first average degradation rate and a second linker capable of degradation at a second average degradation rate. In certain embodiments, the linker degradation is pH dependent. In another illustrative embodiment, the resident structure comprises a first linker capable of degradation under a first set of physiological conditions (e.g., in acidic pH such as in the stomach) and a second linker capable of degradation under a second set of physiological conditions different than the first set of physiological conditions (e.g., in relatively neutral pH such as in the intestines). In some embodiments, the second linker is not capable of substantial degradation under the first set of conditions. For example, in some cases, the second linker is not substantially degradable at a first physiological condition (e.g., in acidic pH such as in the stomach) and is capable of degradation at a second physiological condition different than the first set of physiological conditions.

The term physiological condition generally refers to a set of conditions of the external or internal milleu that may occur in an organism or cellular system (e.g., in contrast to laboratory conditions). For example, in some cases, a physiological condition ranges in temperature between about 20 ° C. and about 40 ° C. (e.g., between about 35 ° C. and about 38 ° C.) and/or atmospheric pressure of about 1 atm. In certain embodiments, the physiological conditions are that of an internal organ such as the stomach, intestines, bladder, lungs, and/or heart.

The linker may be selected such that the linker dissolves, degrades, mechanically weakens, and/or mechanically separates from at least one of the components (e.g., the electronic component, the second component, an arm(s)) after a particular residence time period.

In an exemplary embodiment, the one or more linkers are selected to mediate disassembly of the resident structure after, for example, delivery of an active substance for the residence time period (e.g., after about 24 hours, after about 48 hours, after about one week, after about one month), and safe passage through the lower intestinal tract of the subject. Exit from an orifice such as the gastric cavity may be achieved through changes in the mechanical properties of the linker (e.g., via biodegradation) such that the ability to resist passage through the orifice (or through the pylorus) is compromised, through breakage in the device through designed linker failure.

Several screening tests may be used to determine suitable materials for use as linkers, including but not limited to the ability to interface (e.g., couple) with at least a surface of the one or more components, mechanical strength sufficient to survive encapsulation, and mechanical strength sufficient to undergo the compressive forces present in physiological environments such as the gastric environment. In some embodiments, the linker is stable within a physiological environment such as the gastric environment for a period of time (e.g., a residence time period) of at least about 24 hours, at least about 48 hours, at least about one week, at least about one month, or least about one year.

In certain embodiments, the linker comprises a material such that, under relatively neutral pH physiological conditions (e.g., such as those in the duodenum), the linker can be mechanically broken (i.e. mechanical failure) by a tensile force less than or equal to about 2 N after about less than or equal to about 96 hours, less than or equal to about 48 hours, or less than or equal to about 24 hours under said neutral pH physiological conditions. In some embodiments, the mechanical failure occurs within the linker material itself, and not at the interface between the linker and the one or more polymeric components.

In some embodiments, the resident structure comprises one or more configurations. For example, in certain embodiments, the resident structure has a particular configuration such as a defined shape, size, orientation, and/or volume. The resident structure may comprise any suitable configuration. In some embodiments, the resident structure has a particular shape as defined by a cross-sectional area of the resident structure. Non-limiting examples of suitable cross-sectional shapes include square, circles, ovals, polygons (e.g., pentagons, hexagons, heptagons, octagons, nonagons, dodecagons, or the like), tubes, rings, star or star-like (e.g, 3-armed stars, 4-armed stars, 5-armed stars, 6-armed stars, 7-armed stars, 8-armed stars), or the like. Those skilled in the art would be capable of selecting suitable shapes depending on the application (e.g., a star-like shape for gastric retention resident structures) and based upon the teachings of this specification.

The resident structure may, in some cases, have an original configuration which may be modified (e.g., deformed) such that the resident structure obtains a new configuration, different than the original configuration. For example, in some embodiments, the resident structure has a first configuration and a second configuration, different than the first configuration.

In certain embodiments, the configuration of the resident structure may be characterized by a largest cross-sectional dimension. In some embodiments, the largest cross-sectional dimension of the first configuration may be at least about 10% less, at least about 20% less, at least about 40% less, at least about 60% less, or at least about 80% less than the largest cross-sectional dimension of the second configuration. In certain embodiments, the largest cross-sectional dimension of the second configuration may be at least about 10% less, at least about 20% less, at least about 40% less, at least about 60% less, or at least about 80% less than the largest cross-sectional dimension of the first configuration. Combinations of the above referenced ranges are also possible (e.g., between about 10% and about 80%, between about 10% and about 40%, between about 20% and about 60%, between about 40% and about 80%). Other ranges are also possible.

In some embodiments, the configuration of the resident structure may be characterized by a convex hull volume of the resident structure. The term convex hull volume is known in the art and generally refers to a set of surfaces defined by the periphery of a 3-D object such that the surfaces define a particular volume. In some embodiments, the convex hull volume of the first configuration may be at least about 10% less, at least about 20% less, at least about 40% less, at least about 60% less, or at least about 80% less than the convex hull volume of the second configuration. In certain embodiments, the convex hull volume of the second configuration may be at least about 10% less, at least about 20% less, at least about 40% less, at least about 60% less, or at least about 80% less than the convex hull volume of the first configuration. Combinations of the above referenced ranges are also possible (e.g., between about 10% and about 80%, between about 10% and about 40%, between about 20% and about 60%, between about 40% and about 80%). Other ranges are also possible.

Those skilled in the art would understand that the differences between the first configuration and the second configuration do not refer to a swelling or a shrinking of the resident structure (e.g., in the presence of a solvent), but instead refers to a change in shape and/or orientation of at least a portion of the resident structure (e.g., in the presence of a stimulus such as heat), although some degree of swelling or shrinking may occur between the two configurations.

In some embodiments, the first configuration is constructed and arranged such that a resident structure is retained at a location internal of a subject, and the second configuration is constructed and arranged such that the resident structure may be encapsulated (e.g., for oral delivery of the resident structure within a capsule). In some cases, the first configuration is sufficiently large such that the resident structure is retained at a location internal of the subject and the second configuration is sufficiently small such that the resident structure may fit within a particular size capsule suitable for oral delivery to a subject.

In certain embodiments, the resident structure may be polymerized, printed (e.g., 3D printed) and/or cast in a first configuration, mechanically deformed such that the resident structure obtains a second configuration, and placed in a capsule. The resident structure may be mechanically deformed using any suitable method including, for example, bending, twisting, folding, molding (e.g., pressing the material into a mold having a new shape), expanding (e.g., applying a tensile force to the material), compressing, and/or wrinkling the resident structure. The resident structure may maintain the second configuration for any suitable duration. Advantageously, the resident structures described herein may be relatively stable in the first and/or second configurations such that the resident structure may be stored for long periods of time without significant degradation of mechanical properties of the one or more components and/or one or more linkers. In some embodiments, the resident structure may be stable under ambient conditions (e.g., room temperature, atmospheric pressure and relative humidity) and/or physiological conditions (e.g., at or about 37 ° C., in physiologic fluids) for at least about 1 day, at least about 3 days, at least about 7 days, at least about 2 weeks, at least about 1 month, at least about 2 months, at least about 6 months, at least about 1 year, or at least about 2 years. In certain embodiments, the resident structure has a shelf life of less than or equal to about 3 years, less than or equal to about 2 years, less than or equal to about 1 year, less than or equal to about 1 month, less than or equal to about 1 week, or less than or equal to about 3 days. Combinations of the above-referenced ranged are also possible (e.g., between about 24 hours and about 3 years, between about 1 week and 1 year, between about 1 year and 3 years). Other ranges are also possible.

In some embodiments, the resident structure in the second configuration may recoil such that the resident structure reverts to the first configuration. For example, in some embodiments, the resident structure in the second configuration is contained within a capsule and delivered orally to a subject. In some such embodiments, the resident structure may travel to the stomach and the capsule may release the resident structure, upon which the resident structure obtains the first configuration.

As described herein, in some embodiments, the resident structure may comprise one or more components with particular mechanical properties such that the resident structure will substantially recoil after being mechanically deformed (e.g., an elastic core). The resident structure may be characterized, in some cases, by a folding force. The term folding force generally refers to the force required to compress the resident structure into a cavity having a cross-sectional area of less than about 2 cm (e.g., such as the pylorus). In some embodiments, the folding force of the resident structure is at least about 0.2 N, at least about 0.5 N, at least about 0.7 N, at least about 1 N, at least about 1.5 N, at least about 2 N, at least about 2.5 N, or at least about 3 N. In certain embodiments, the folding force of the resident structure is less than or equal to about 5 N, less than or equal to about 3 N, less than or equal to about 2.5 N, less than or equal to about 2 N, less than or equal to about 1.5 N, less than or equal to about 1 N, less than or equal to about 0.7 N, or less than or equal to about 0.5 N. Combinations of the above-referenced ranges are also possible (e.g., between about 0.2 N and about 3 N, between about 0.2 N and about 2.5 N, between about 0.5 N and about 1.5N, between about 1 N and about 3 N). Other ranges are also possible. The folding force may be determined by, for example, by placing the resident structure in a funnel having a 20 cm upper diameter and a 2 cm lower diameter (e.g., simulating the pyloric sphincter) and measuring the forces required to move the resident structure through the 2 cm lower diameter. A plunger may be attached to the tension cross-head of an tensile loading machine and the funnel to a clamp, and the resident structure pushed through the funnel at a rate of, for example, 10 mm/min, which measuring the force and displacement. The folding force is generally determined by measuring the force at which the resident structure folds and enters the 2 cm lower diameter tube.

In certain embodiments, the resident structure in the first configuration has a minimum uncompressed cross-sectional dimension. The minimum uncompressed cross-sectional dimension is generally selected such that the resident structure is retained at a location internally to a subject for a relatively long period of time (e.g., at least about 24 hours) even under physiological compressive forces (e.g., such as those in the digestive tract).

In some embodiments, the minimum uncompressed cross-sectional dimension of the first configuration is at least about 2 cm, at least about 4 cm, at least about 5 cm, or at least about 10 cm. In certain embodiments, the minimum uncompressed cross-sectional dimension of the first configuration is less than or equal to about 15 cm, less than or equal to about 10 cm, less than or equal to about 5 cm, or less than or equal to about 4 cm. Combinations of the above-referenced ranges are also possible (e.g., between about 2 cm and about 15 cm). Those skilled in the art would be capable of selecting suitable minimum uncompressed cross-sectional dimensions for resident structures based upon the teachings of this specification for specific orifices of a subject such that the resident structure is retained.

As described herein, in some embodiments, the one or more components of the resident structure may be cast, molded, 3D printed, and/or cut to have a particular shape, size, and/or volume.

In an exemplary embodiment, a shape capable of residence (e.g., being retained in an orifice at a particular location internal to a subject) such as gastric residence comprises a three-dimensional structure having a plurality of projections (i.e. arms). In some embodiments, the structure with projections comprises a flexible material capable of elastic (non-plastic) deformation. The projections themselves may be flexible or rigid with flexible connections to a core. In some embodiments, one or more controlled degradation linkers (e.g., enteric elastomers) are attached to and/or incorporated into the structure, for example, along one or more projections, preferably near or at the connection to a core. In some embodiments, each projection has a length equal to just less than the length of a soluble container such that the unencapsulated final form has a diameter equal to nearly twice the soluble container length. In some embodiments, the projections each have a length of about 0.5 cm to about 2.5 cm (e.g., such that the resident structure has a minimum uncompressed cross-sectional dimension of at least about 2 cm).

In certain embodiments, the projections are arranged based on bio-inspired flower bud designs in which a number (N) of radial spokes or petals project from a central linking core. In some embodiments, these radial projections each have an internal sector angle of approximately 360°/N, where N is the total number of radial projections. In some cases, this maximizes the packing volume of the encapsulated structure, thus maximizing drug carrying capacity. In some embodiments, the projections are formed of a material with a relatively high elastic modulus to increase the resistance to compression and duration of gastric residence, as described herein.

According to some embodiments, a shape capable of residence (e.g., being retained in an orifice at a particular location internal to a subject) such as a gastric residence comprises a three-dimensional structure forming a polygon outline with, for example, 3, 4, 6, 8, 10, 12, 14, 16, 18, or 20 sides, when projected onto a flat surface. In some embodiments, each side has a length equal to just less than the length of a soluble container. In some embodiments, the structure comprises a flexible material capable of elastic (non-plastic) deformation such that the structure is capable of bending at its vertices and packing into a soluble container. Materials with low elastic moduli, with low creep deformation and/or good recoil, and capable of large elastic deformation may be used at the vertices to facilitate stable packing. In some embodiments, individual sides each have an internal sector angle of approximately 360 °/N, where N is the total number of sides, to obtain maximal packing.

As described herein, in some embodiments, the resident structure is configured to adopt a shape and/or size compatible with oral administration to and/or ingestion by a subject. In some embodiments, the resident structure has a shape with a capacity for folding and/or packing into stable encapsulated forms. For example, in some embodiments the resident structure is designed to maximally pack and fill a capsule or other soluble container (e.g., a containing structure). In some embodiments, the resident structure has a shape that maximally fills and/or packs into a capsule or other soluble container.

In some embodiments, the system comprises the resident structure and a containing structure. Based on the application, a capsule may be manufactured to particular specifications or a standard size, including, but not limited to, a 000, 00, 0, 1, 2, 3, 4, and 5, as well as larger veterinary capsules Su07, 7, 10, 12el, 11, 12, 13, 110 ml, 90 ml, and 36 ml. In some embodiments, the resident structure may be provided in capsules, coated or not. The capsule material may be either hard or soft, and as will be appreciated by those skilled in the art, typically comprises a tasteless, easily administered and water soluble compound such as gelatin, starch or a cellulosic material.

In other embodiments, the resident structure is retained in a packed shape by a soluble retaining element, such as a band or surgical thread. In some embodiments, the resident structure comprises optimal combinations of materials with high and low elastic moduli, giving the resident structure the capacity to alter its shape and/or size once the soluble container and/or soluble retaining element is removed.

In some embodiments, the resident structure comprises one or more features described in U.S. Provisional Application Ser. No. 62/591,556, filed Nov. 28, 2017, the contents of which are incorporated herein by reference in its entirety for all purposes.

Any terms as used herein related to shape, orientation, alignment, and/or geometric relationship of or between, for example, one or more articles, compositions, structures, materials and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described.

EXAMPLES

The following examples are intended to illustrate certain embodiments of the present invention, but do not exemplify the full scope of the invention.

Long-term implantation of biomedical electronics into the human body generally enables advanced diagnostic and therapeutic functionalities. However, most long-term resident electronics devices require invasive procedures for implantation as well as a specialized receiver for communication. Here, a gastric resident electronic (GRE) system (i.e. a resident structure comprising an electronic component) is presented that leverages the anatomical space offered by the gastric environment to enable residence of an orally delivered platform of such devices within the human body. The GRE is capable of directly interfacing with portable consumer personal electronics through Bluetooth, a widely adopted wireless protocol. In contrast to the passive day-long gastric residence achieved with prior ingestible electronics, advancement in multi-material prototyping enables the GRE to reside in the hostile gastric environment for e.g., 36 days and maintain e.g., ~15 days of wireless electronics communications as evidenced by studies in a porcine model. Indeed, the synergistic integration of reconfigurable gastric-resident structure, drug release modules and wireless electronics could ultimately enable the next-generation remote diagnostic and automated therapeutic strategies.

The integration of electronics with the human body has the potential for significant impact on novel personalized diagnostic and treatment strategies. For instance, the creation of wearable electronics has enabled real-time interfacing of digital devices with the body to measure physiological parameters such as heart rate, respiratory, oxygen saturation, blood pressure and glucose level. Implantable electronics have enabled a broad set of capabilities including electrical stimulation of several organs including the heart, the gastrointestinal tract, and the brain, as well as monitoring of physiologic parameters including cardiac and gastrointestinal. Moreover, several technologies including systems allowing externally controllable drug release in the form of microchips as well as pump systems are in various stages of development. All these systems generally require a range of significant intervention ranging from needle-based access to surgical implantation. Furthermore, long-term surgically placed medical implants are associated with eliciting foreign body immune responses. In addition, implanted devices can serve as a nidus for infection which can require immediate operative intervention.

Oral delivery remains a desirable route for drug delivery and is an intuitive, appealing but relatively unexplored method of transiently implanting long-term resident electronics. Oral delivery can leverage the significant space and immune-tolerant environment available within the gastrointestinal tract, circumventing the needs for more invasive device placement. This method, coupled with a unique design, optimized set of materials and the capacity to control the macrostructure may obviate the potential health risks often associated with surgical implantation. The stomach generally represents an immune privilege site in the body with a holding volume of approximately 1.5 liters without significant distention. The stomach is an organ that has evolved to digest a large volume of food and as such it has a relatively higher tolerance for foreign materials. Pathophysiologic examples of the tolerance of the stomach for resident objects have been documented for centuries in the form of bezoars. These aggregates can form from many materials and generally manifest in gastrointestinal outlet obstruction symptoms when they reach a mass in excess of ~50 g. Long-term (>1 week) larger devices have been applied successfully to the stomach for bariatric intervention. Gastric resident systems in ingestible formats are in various stages of pre-clinical and clinical development and are being applied for drug delivery supporting the capacity of this environment to sustain a range of materials and even drugs for prolonged periods of time.

The delivery of electronics through ingestion is an exciting concept that has been explored since 1957. Recent developments in ingestibles have noted a myriad of functionalities, incorporating temperature, pH, pressure, or biomolecular sensors, wireless identification microchip, gas sensor, camera for wireless imaging and endoscopy or drug delivery modules. Nevertheless, these ingestible electronics are incapable of maintaining a stable long-residence in the stomach. Most demonstrations to date are limited to a passive, uncontrolled gastric transit with a period of less than a week, which limits the potential application of ingestible bio-electronics to transient diagnostics and therapeutic strategies.

Figure 2A:
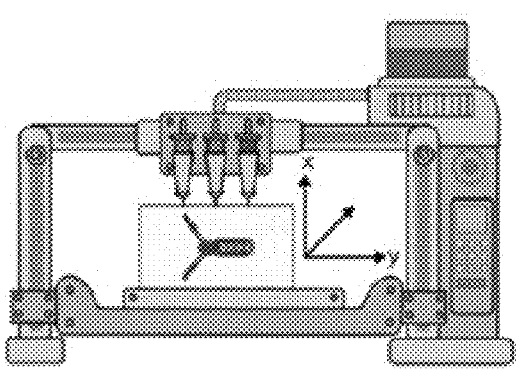
FIGS. 2A-2J show 3D Printed Gastric Resident Electronics (GRE) for biomedical applications, according to one set of embodiments. Illustration describes the 3D printed GRE concept.
Figure 2B:
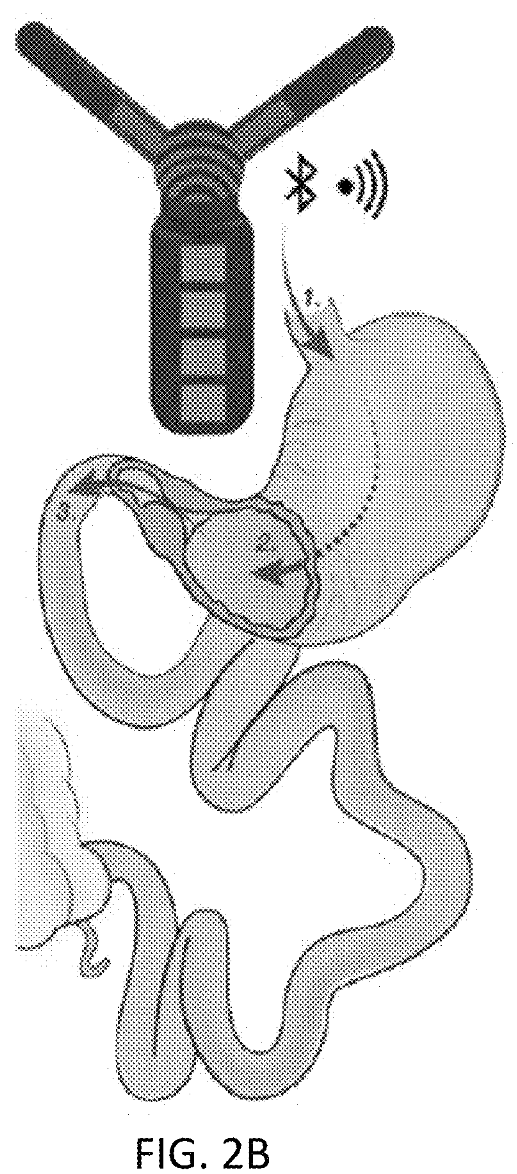
Figures 2C, 2D, 2E, 2F, 2G:
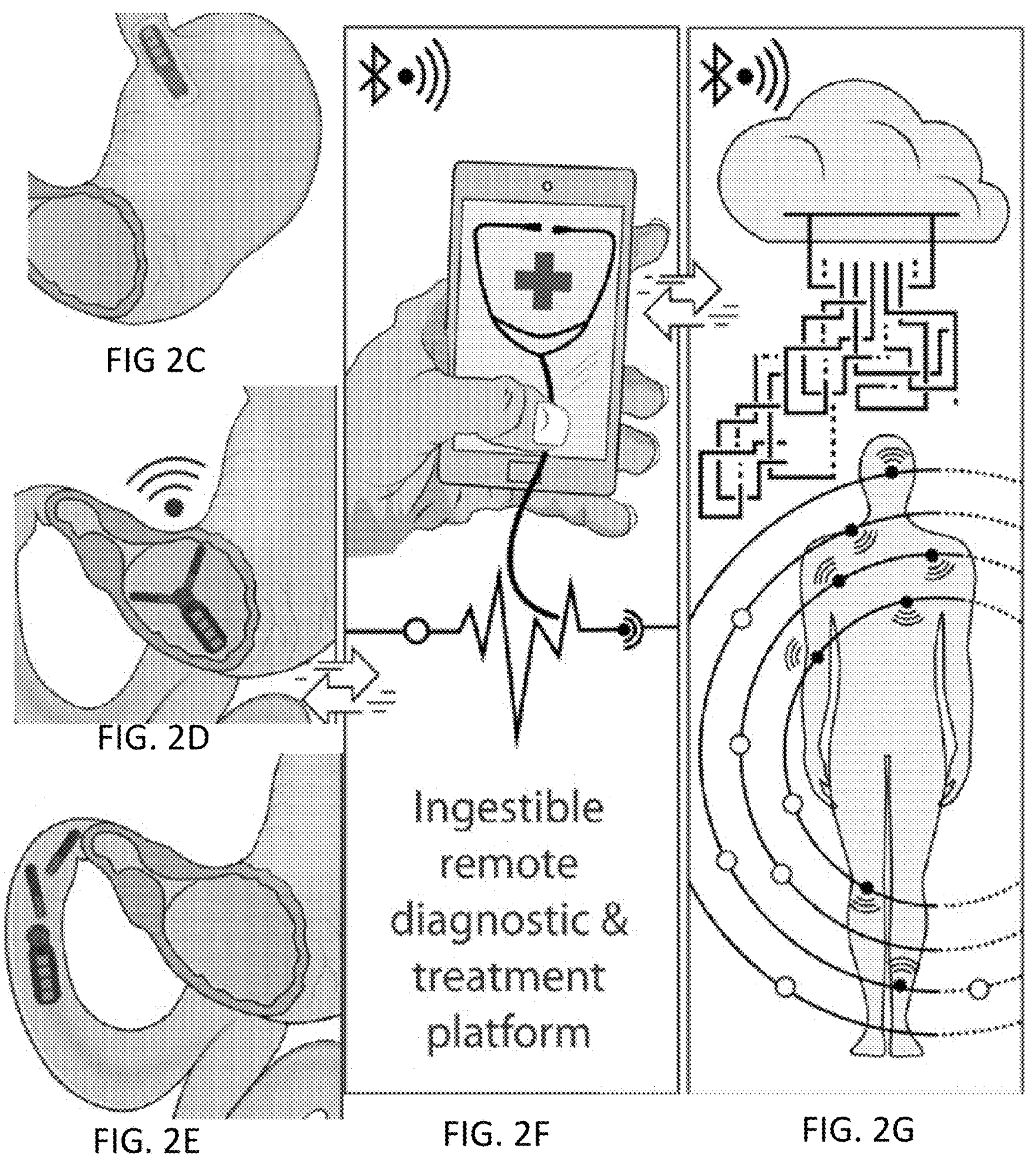

The design and manufacturing of a wireless gastric resident electronic (GRE) device described herein (i.e. an electronic resident structure) that can achieve in vivo gastric residence in a porcine stomach for up to and including of 36 days and maintaining in vivo wireless communication for up to and including 15.3 days. Controlled-released formulation of drugs (antimicrobial and hormonal agents) were synthesized that can be co-integrated in the drug delivery module to enable the simultaneous controlled-release of drugs. A customized multi-material 3D printing of gastric residence architecture allows a seamless integration of wireless electronics, transformable multi-materials structure and drug delivery reservoirs, as shown in FIG. 2A. The GRE is designed to be delivered orally into the stomach (1), reside in the stomach (2) pass through the pylorus (3) and be excreted out of the body. The device can be folded into an ingestible dosage form for delivery via the oral tract, as described in FIG. 2C. Upon reaching the stomach, the system expands to a geometry with an effective diameter that is larger than the pylorus (a measured maximum diameter of 1.9 cm) to enable the residence of the device in the gastric space as shown in FIG. 2D. This coupled to the mechanical properties of the central flexible element (See FIG. 6) enables gastric residence and allows long-term remote communication with a personal device.

Ultimately, the passive disintegration of the device or potential triggered disintegration allows the passage of the device from the gastric cavity as illustrated in FIG. 2E. The extended residence property of the gastric electronics can potentially help realize the next generation of digital diagnosis and treatment strategies. For instance, as described in FIG. 2F, GRE can be compatible with personal electronics, such as the smart phone, enabling the users and health care providers to directly communicate and control the GRE through Bluetooth connection without specialized equipment. This compatibility also allows a seamless interconnection with other wireless electronic peripherals, wearable devices and biomedical implants, facilitating a real-time feedback-based automated treatment or responsive medication. Further, as illustrated in FIG. 2G, the interconnection of GRE with the digital cloud via personal electronics could ultimately enable remote health management and monitoring as well as personalized and large population data collections for clinical studies.

Several fundamental challenges had to be overcome before realizing the GRE. First, the device may be able to transform from an ingestible dosage form to an expanded configuration immediately upon the entry into the stomach. Second, the GRE may be able to maintain its gastric residence property within the mechanically and chemically hostile gastric environment and have the capacity to be triggered to breakup into subcomponents to enable gastrointestinal transit in the event of an adverse reaction. Third, GRE may be compatible with a widely adopted wireless communications protocol (e.g. Bluetooth) and be capable of maintaining long-term (beyond a day) communications with personal electronics devices. Indeed, such level of integration has not been demonstrated with prior ingestible devices, partly due to the limitation in the versatility of design and integration of conventional manufacturing method such as molding.

Figure 2H:
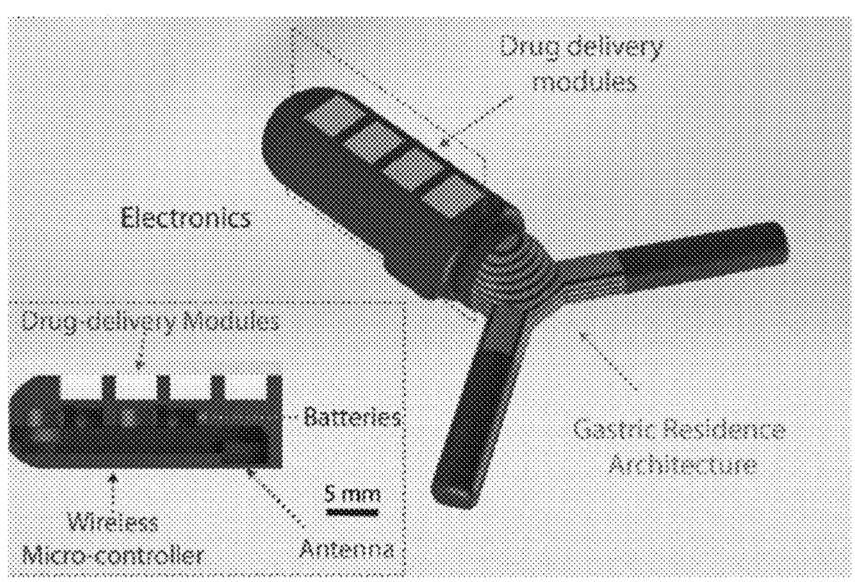

These challenges were generally overcome with a unique three-dimensional, heterogeneous design enabled by multimaterials additive manufacturing. Specifically, a wireless remotely controlled drug-release module was designed integrated with a two-armed gastric residence architecture that can transform between a compressed dosage form to an expanded form (FIG. 2H). The robustness of the device is tailored to achieve a prescribed gastric residence with the dynamic gastric environment. This hybrid integration approach leverages the versatility of additive manufacturing design methodology, and enables the seamless incorporation of gastric residence architecture with active modules such as personalized drug delivery modules, wireless electronics, antenna and power systems to achieve a long-term in vivo communications and drug-delivery.

Prior successful gastric resident architectures generally rely on synthesized materials with a similar chemical basis to maintain strong interfacial strength between the elastomeric and stiff component. Here a layer-by-layer 3D printing of elastomeric and stiff polymer to significantly amplify the adhesion strength between the two different classes of materials was chosen that would otherwise be fragile in a dynamically hostile gastric environment. In order to accommodate commercially available wireless electronic components, a three-armed based system was developed for gastric residency. The freeform fabrication of a robust transformable architecture prototype with Fused Deposition Modeling (FDM) based on commercially available thermoplastic filaments was first investigated (see FIG. 3A). Specifically, the exemplary gastric resident architecture is created with a bio-compatible poly-1-lactic acid (PLA) and a thermoplastic polyurethane (NinjaTek NinjaFlex® 85A). The gastric-residence architecture prototype is designed with the maximum compressed thickness that fits into a 000 size capsule (hereafter referred to as GRA).

Figures 3A, 3B:
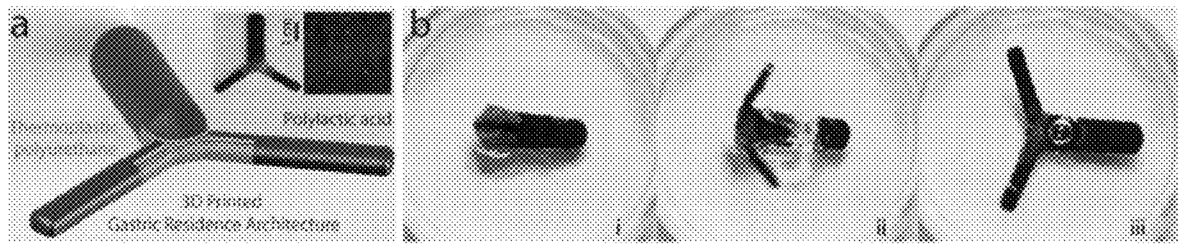
FIGS. 3A-3G show 3D printed multi-material gastric-residence architecture prototype (GRA) and electronics (GRE), according to one set of embodiments.

The re-configurable structure (i.e. the GRA) generally allowed the transformation from an ingestible form to an expanded form in the stomach. The structure can be folded into a gelatin capsule that can dissolve in the stomach acid. Upon the dissolution, it expands to an effective diameter that is larger than the diameter of pylorus, which coupled to the mechanical properties of the multi-layered flexible center, enables gastric residency (See FIG. 6). As shown in FIG. 3B, the expansion was rapid (within 50 seconds) upon full immersion in simulated gastric fluid, independent of the orientation of the device. Next, the GRA was embedded with stainless steel imaging probes (1 mm beads) to enable X-ray visualization of the printed device inside the gastric cavity (see inset FIG. 3A). Specifically, three metal fiducials were inserted to indicate the location of the potential electronics chipset (hereafter referred to as "head"), and two metal fiducials to indicate the two thinner "arms" supporting gastric residence architectures (hereafter referred to as "arm"). This allowed for the measurement of the gastric residence period by monitoring the potential electronics site (head) as well as the structural integrity of the printed multi-material prototype without an endoscopy procedure. The gastric residence period in this case was the maximum time the "head" is detected on X-ray. It was noted that there is an imaging gap in some of the studies due to the limitation of maximum possible X-ray frequency under approved animal protocol.

Figures 3C, 3D:
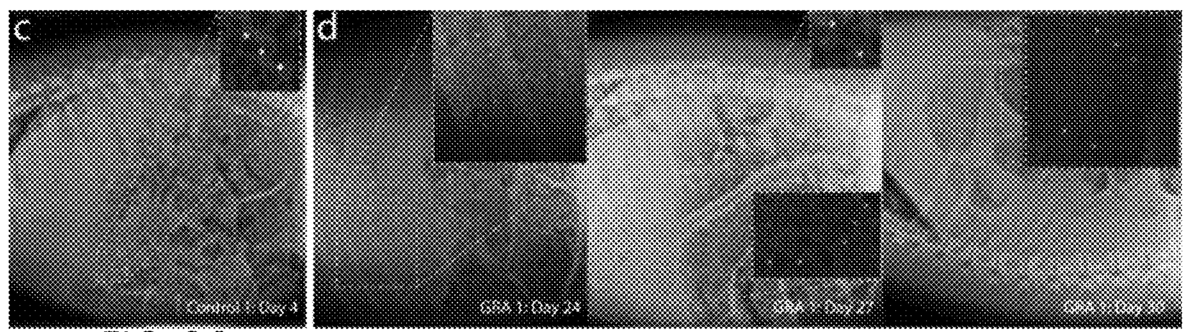

Control experiments were conducted through evaluation of the gastric residence period of the electronics "head" without the gastric residence architecture. This is a critical consideration to account for the slower gastric motility of a porcine model. It is noted that the maximum gastric residence period achieved without GRA is three days, as shown in FIG. 3C. In contrast, the GRA significantly prolonged the gastric residence. The GRA remained intact after 24 days in the gastric environment, as shown in FIG. 3D (left). Next, the disintegration of the prototype was evaluated. In two of the four samples, images of the failure were captured that shows the prototype detachment of "arms", which eventually causes the passage of the GRA from the gastric space. As shown in FIG. 3D (center), the GRA structure disintegrated via the initial detachment of one of the two arms, as indicated by the metal probes at day 27. On day 30 (FIG. 3D right), both the GRA arms had been detached, which ultimately caused the GRA to pass from the gastric space within 34 days.

In one of the four studies, a premature passage of the GRA was observed on day seven without disintegration. One of the four samples' failure mechanism was not captured due to the imaging frequency limited by the animal protocol. Nevertheless, no clinical complication (such as intestinal obstruction) was observed in the experiments, indicating that GRA was passed safely. This can potentially be attributed to the fenestrated open macro-structure of the GRA that reduces the likelihood of intestinal blockages, in contrast to prior clinical complications observed with closed macro-structures of polyurethane foams.

Figure 7:
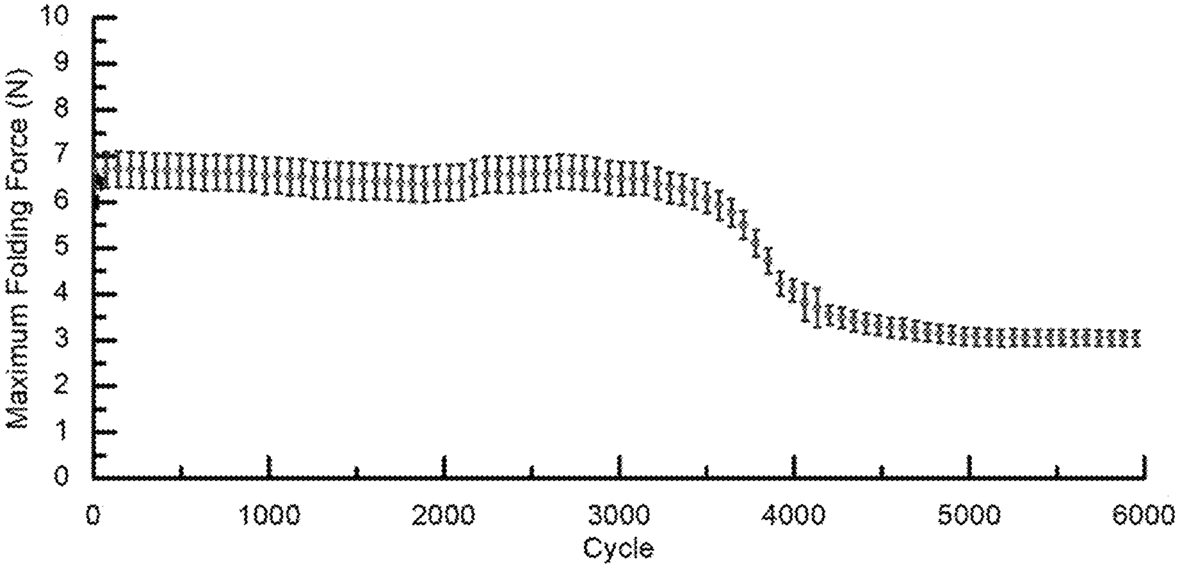
FIG. 7 shows a plot of the maximum folding force measured with funnel test apparatus to simulate the passage of PCL-PLA GRA through pylorus, according to one set of embodiments. The measurement was repeated for 6000 cycles to evaluate the fatigue properties. Note that only 1 out of 70 points is plotted in this graph to clearly illustrate the standard deviation.

An approach to incorporate a thermoset polymer by first co-printing with water-soluble polyvinyl alcohol (PVA) polymer, and subsequently replacing the PVA with the thermoset elastomeric polymer, was also demonstrated. As a proof of concept, a PCL-PLA based GRA was created, which demonstrates the potential for future work to incorporate a thermoset polymer (See FIG. 7). pH-responsive enteric elastomer, which can dissolve in the neutral-pH environment of the small and large intestine, are also possible.

Figures 8A, 8B, 8C:
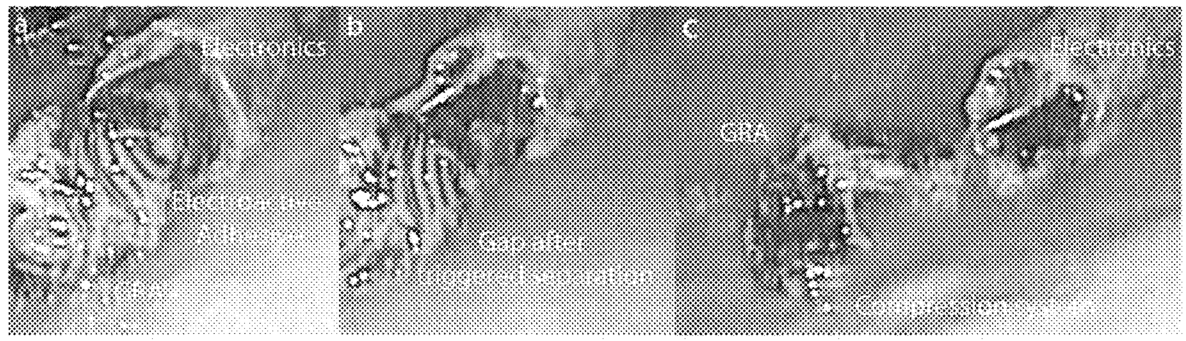
FIGS. 8A-8C show photographs of triggerable GRE device separation, according to one set of embodiments.

Additionally, prototypic modes of external triggering of dissolution of linker segments were developed in the event that macro-structure dissolution may be required should a subject develop an adverse reaction to a device (See FIGS. 8A-8C).

Figure 2I:
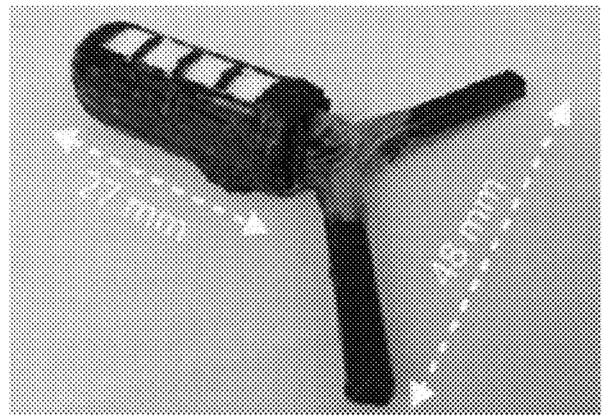
Figure 2J:
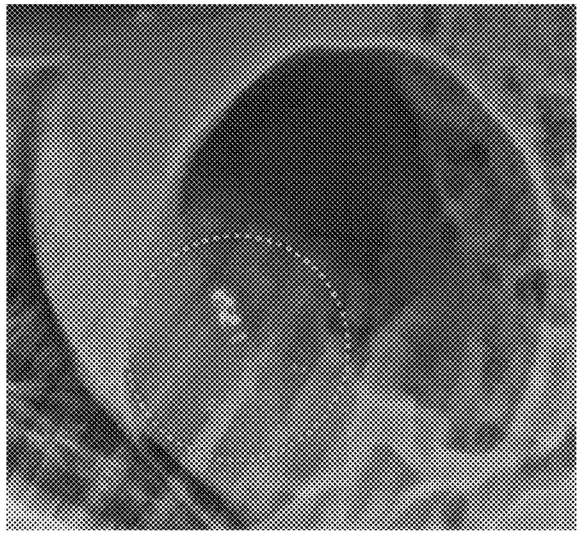

Based on the in vivo experiments conducted with the GRA, dimensions were increased as indicated in FIG. 2I. It is noted that the minimum size of the head of the GRE is larger in comparison to the GRA to accommodate the minimum size of the electronics chipset design possible without circuit board components integration. Indeed, the electronic prototype board can be readily miniaturized with a chipset repackaging. Similar to the approach with GRA, stainless steel fiducials were embedded in the arms (one to two per arm) to visualize the integrity of the arms in the electronic device. The integrity of the electronics was observed directly using X-ray imaging. It was observed that the integrated gastric GRE exhibited an overall longer gastric residence period, which is hypothesized is due to the increase of size. The disintegration of the GRE was similar to that of the GRA. The two arms of the device detached on Day 24 and 31 and the device passed out of the gastrointestinal tract within 41 days. It is noted that the maximum gastric residence period of GRE achieved was 36 days, out of three samples.

Figures 3E, 3F, 3G:
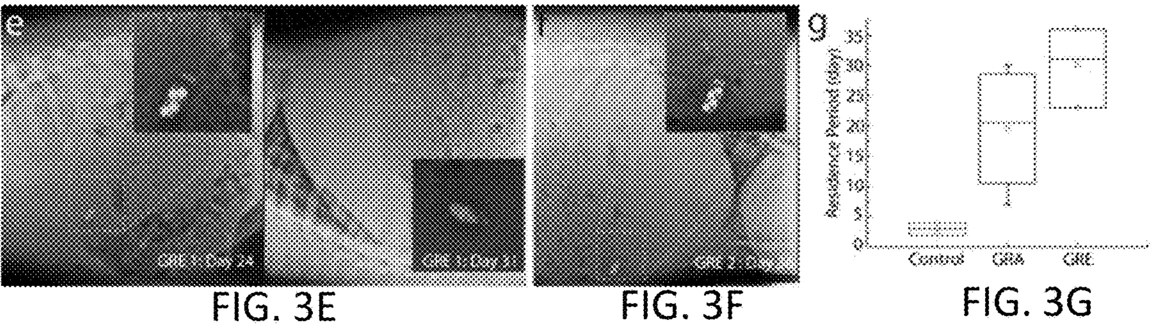

The in vivo experiments with swine models demonstrate the ability of the prototype to sustain the mechanical stress in a large animal model. It is noted that variation of gastric residence period between samples is likely due to inherent inter-animal variation. In general, both GRA and GRE demonstrate a significant increase in gastric residence period in comparison to the electronics as shown in FIG. 3G. The maximum period of gastric residence is 30 days and 36 days respectively, in comparison to a maximum residence of three days for the structure without the gastric residence architecture.

Figures 4A, 4B, 4C, 4D:
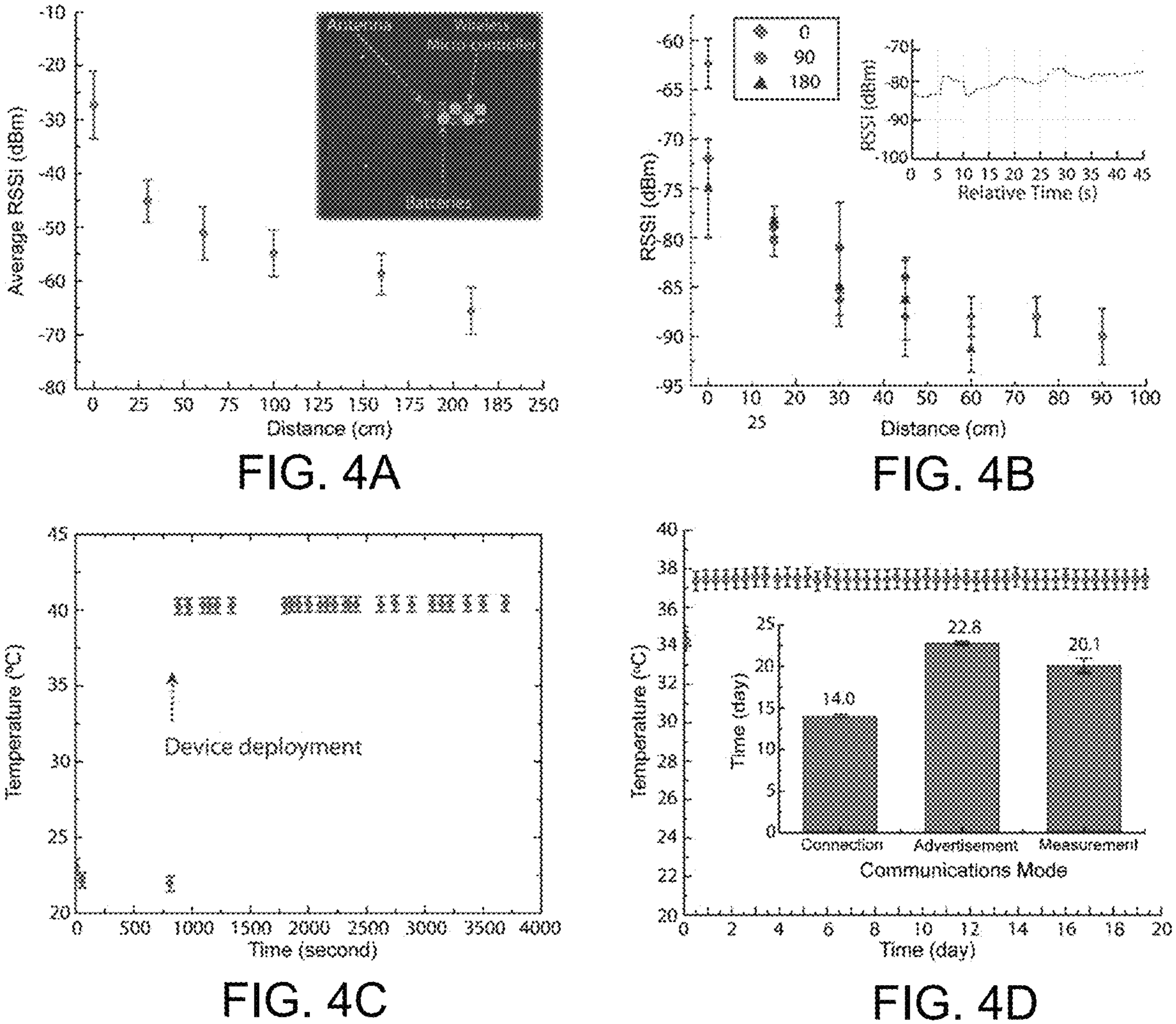
FIGS. 4A-4D show wireless performance and lifetime of gastric-residence electronics, according to one set of embodiments.

The ability to achieve a month-long residence with a three-armed gastric residence architecture enables the incorporation of active modules, which has not been previously demonstrated in gastric resident systems. For instance, as illustrated in FIG. 2H, a wireless Bluetooth radio-frequency chipset, antenna, batteries and drug delivery modules can be integrated into the device via a hybrid integration approach. The functioning electronics is readily capable of establishing wireless connection via a standard, widely adopted 2.4 GHz Bluetooth radio-frequency protocol. The signal strength was characterized in vitro as shown in FIG. 4A, where devices exhibited an average signal strength of −45 dBM at 30 cm, without power amplification (+0 dBM). The signal strength was then assessed while the device resided in the stomach, as shown in the in vivo experiments in FIG. 4B. The distance was measured relative to the surface of the stomach of the pig in three directions to evaluate the directionality of the signal strength. The changes in signal strength at different angles in vivo is expected due to the asymmetric nature of organs. Nevertheless, despite the attenuation at 2.4 GHz transmission frequency caused by the tissue and fat surrounding the gastric cavity of a large animal (35-58 kg Yorkshire pig), it was shown the ability to maintain a stable interconnection with an off-the-shelf personal electronic device without additional hardware enhancement (electronics tablet and smart phone) (inset of FIG. 4B). The ability to seamlessly interconnect with a user's devices and simultaneously restrict the signal strength to within an arm's length (e.g. −80 dBM to −90 dBM at 45 cm) was demonstrated. The limited connection range is a desirable security enhancement. The self-isolation of wireless signal strength within the user physical space could shield the device from unwanted connections, providing a physical isolation for additional security and privacy protection. Having validated the ability to receive advertised packets from the GRE, in vivo experiments were then performed to validate the ability to form bilateral Bluetooth connections with the GRE. This is demonstrated with a smart phone by directly connecting and requesting temperature measurement operations and receiving the temperature-sensing data from the GRE residing in the stomach of a Yorkshire pig. FIG. 4C shows the increase in temperature from room temperature to core-body temperature of a pig.

The integration of GRE with sensing elements could enable the creation of a long-term resident diagnostic platform. Having validated the ability to establish interconnection with the GRE in the pig, prolonging the device lifetime to achieve multi-week-long wireless functionalities was next addressed. For example, the communication protocol was optimized to prolong the GRE communication lifespan. The goal is to maximize GRE lifetime by reducing power consumption without compromising the device's ability to establish and maintain wireless interconnection with personal electronics. As shown in the inset of FIG. 4D, the lifetime of GRE under “Connection” and “Advertisement” modes with a minimum functional communication frequency were compared. For instance, configuring the advertisement interval to ten seconds enabled the GRE broadcasting lifetime to an average of 22.8 days under in vitro conditions. Further increases in advertisement interval beyond ten seconds would result in challenges in establishing a stable Bluetooth connection. Conversely, a reduction of the interval could result in the decrease of device lifetime. Based on the experimental result, an Android communication protocol was designed to (1) seek the advertisement signal of a GRE based on the device unique identifier (media access control address, MAC address); (2) establish Bluetooth connection; (3) request temperature measurement to the GRE; (4) acquire and store temperature data in the Android platform and (5) disconnect the GRE. This cycle is then repeated at a prescribed measurement interval. This enables the GRE to only establish connection as needed reducing overall power consumption by resuming to the low power advertisement mode until the next measurement point. As a proof of concept, as demonstrated in FIG. 4D the ability to prolong the measurement to an average lifetime of 20.1 days for three GRE devices in an in vitro setting. A slight reduction in communication lifetime was observed when the device was configured to perform temperature measurement. This is expected due to the additional energy consumed in establishing connections, as shown in the FIG. 4D inset.

Figures 5A, 5B, 5C, 5D:
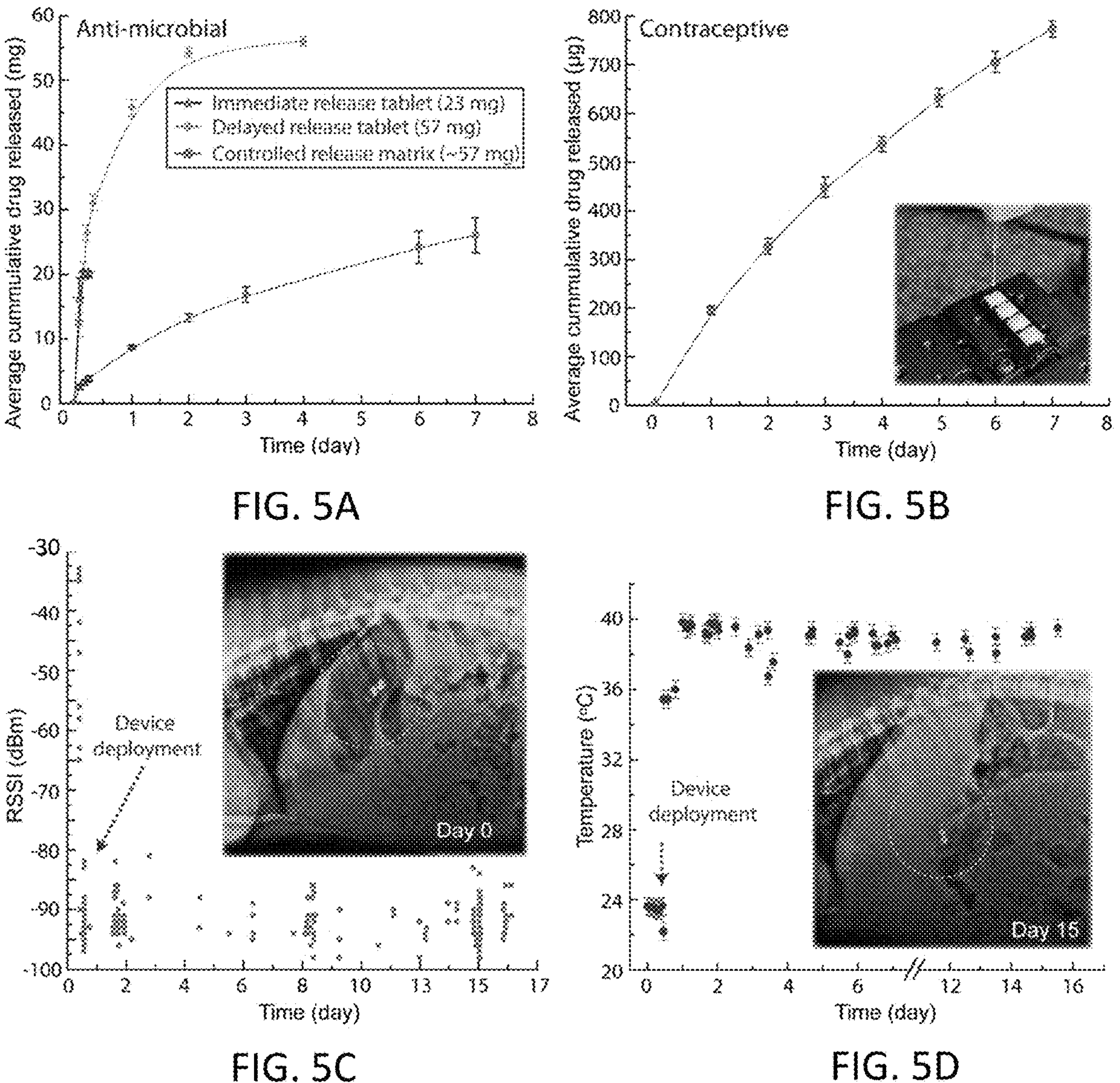
FIGS. 5A-5D show drug delivery and remote sensing with gastric-residence electronics, according to one set of embodiments.

The GRE architecture allows the integration of a drug delivery module, enabling the simultaneous controlled-release of drug during electronic sensing and operations. The ability to integrate a controlled release formulation of an antibiotic drug (doxycycline), is shown in FIG. 5A. Drug release from this sustained release formulation of doxycycline was tested, and compared it to immediate release and delayed release tablets. Drug release from the immediate release tablet in simulated gastric fluid was rapid. Almost all of the contents were released in less than 30 minutes. Drug release from the delayed release tablet lasted longer and a significant portion (~80%) of the drug was released within 24 hours. In contrast to tablets that are retained in the gastrointestinal tract for 1-2 days, the GRE is retained in the stomach for several weeks. Hence, drug release from the GRE is intended to be prolonged. To achieve this, doxycycline was loaded in a hydrophobic biodegradable matrix made of PCL. Drug release from the PCL matrix was gradual. After an initial burst of ~10% in the first 0.5 h, drug was released at a near constant rate. Twenty-five milligrams of the drug were released over one week. While this dosage is below the clinically efficacious dose, it serves as a proof-of-concept for sustained drug release using the GRE device.

It is also noted that the entire drug-delivery device fabrication process is compatible with a desktop 3D printing process. As a proof-of-concept, a printable levonorgestrel releasing silicone matrix [poly(dimethylsiloxane)] (PDMS) was 3D printed into the GRE structure. It was demonstrated that with the integration of a controlled-release formulation, levonorgestrel is released over a course of six days with an average of 106 μg per day. FIG. 5B shows the average cumulative drug release profile in simulated gastric fluid. Inset of FIG. 5B shows the 3D printing of the formulated drug into 3D printed drug wells. Such long-resident release of hormone could function as a long-resident hormone therapy platform, or to function as an ingestible contraceptive platform.

The wireless connectivity of the GRE can be leveraged to incorporate various electrically activated modules. GRE is compatible with a wide-range of actuation principles and can be designed based on the electrical power system affordable. Indeed, such a platform can be designed to achieve an electrically modulated drug delivery in addition to tailoring the polymeric matrix to achieve a range of drug release profiles demonstrated earlier. For example, triggerable drug delivery with gold membranes is achievable.

In another example, electrically activated modules through implementation of electroactive adhesive can potentially be developed to achieve drug delivery by micro-compounding low melting temperature polymer with electrically conductive nanomaterials. (See FIGS. 9A-9C, as well as the detail synthesis of the electroactive adhesive). Unlike molding, 3D printing allows the co-integration of drugs formulated with distinct programmable release profile. This allows a seamless digital manufacturing methodology of long-resident drug delivery device. It is envisioned that such rapid prototyping approach could enable the on-demand digitally defined creation of drug delivery GRE device at a local healthcare facility by physicians and pharmacists, allowing next generation personalized treatment strategies.

Indeed, the GRE is designed with a widely-adapted Bluetooth communication protocol and can interconnect with other clinical equipment, wearable or implantable sensors. The synergistic integration of electrically modulated drug release and device interconnection offers an exciting means of achieving digital-based biomedical diagnosis and intervention. It is anticipated that the coupling of drug delivery modules with the advancement of on-body or implanted bio-sensors could ultimately enable a rapid, automated or on-demand drug intervention to eliminate opportunistic infections prior to their growth and spreading as well as other applications where closed loop systems can help maximize the efficacy of an intervention on a clinical outcome.

As a proof of concept, multi-week-long physiological monitoring was demonstrated, such as core body temperature measurement, with a personal electronics compatible system via the GRE platform. This is achieved by integrating the three core-advancements described earlier. First, the capability of the device to reside in the gastric space for a month (FIGS. 3A-3G). Second, the capability of establishing a direct, bilateral Bluetooth communications between commercially available personal electronics and the GRE residing inside the stomach of a large animal (FIG. 4B-4C). Third, the ability to prolong the GRE wireless electronics to weeks (FIG. 4D). The integration of these core-developments ultimately realize the demonstration of multi-week-long core-temperature measurement of a porcine pig model, as shown in FIG. 5C and FIG. 5D. It was noted that the data gap recorded is due to the required physical clearance between the personal electronics (Android tablet) attached to the cage of the porcine model. This causes the GRE to be outside the range of connection (larger than 75 cm) when the porcine subject can move freely around the cage. Specifically, the Android tablets are attached at the wall of the cage with an area of 1.52 m×1.52 m, and the tablet is placed 1.49 m above the ground. The distance is necessary to minimize the disruption of animals' daily routine and to prevent the disruption of tablet operation. It was noted that establishing connection was successful with the GRE despite the distance, which falls at the weaker range (−100 dBm to −80 dBm) as shown in FIG. 4B. Such constraint will not generally be applicable in a human user where the personal electronics are used within the operational range.

The GRE demonstrated a 15.3 day operational lifetime inside the porcine stomach (FIG. 5D). It is noted that the batteries were encapsulated within the device with a biocompatible polymer, poly(lactic acid) (PLA), to eliminate the potential risk of injury due to either the corrosive action or electrical burn upon contact with the GI tract. Further, unlike commonly used lithium-ions based batteries with higher maximum current, the small (4.8 mm in diameter) silver oxide battery generally has a significantly lower likelihood of residence. In addition, it rapidly developed internal resistance during a short-circuit event, which self-limits its maximum output current in the unlikely incidence of battery contact with the GI tract. A single coin cell short circuit current is limited to a transient (orders of 4 seconds) spike of a short-circuited leakage current that is less than 22 mA. It is noted that the demonstrated lifetime is shorter than the gastric residence period as shown in FIG. 3G, due to the limited energy capacity that can be accommodated by batteries in a limited size. It is anticipated that with further advancement of integration, GRE can be powered by chemical energy harvested from gastric fluids, biodegradable batteries system and/or a wireless powering mechanism to safely prolongs the device functionality in the hostile in vivo gastric environment.

In summary, the non-surgical and needle free transient implantation of wireless gastric resident electronic devices into the body has the capacity of providing a remote, direct diagnostic and therapeutic intervention. The ability to directly interface with portable consumer personal electronics such as smart phones, tablets and devices through a widely adopted wireless protocol empowers the users to directly communicate and control the long-residence gastric device without surgical procedures or other specialized equipment. This also enables a seamless interconnection with other wireless electronics peripherals, wearable devices and biomedical implants, enabling a real-time feedback-based automated treatment or responsive medication. Indeed, the interconnection of ingestible gastric-resident electronics with the digital cloud via personal electronics could enable remote health management and monitoring as well as data collections for clinical studies. Ultimately, the ingestible gastric residence electronics provides a needle and surgery free approach to synergistically integrate biomedical electronic devices, the human body and the digital domain—realizing next-generation remote diagnostic and automated therapeutic strategies.

Gastric Residence Architecture Prototype (GRA) fabrication: 3D Computer Aided Design (CAD) models of GRA as shown in FIG. 3A were first created with Solidworks 2016 (Dassault Systemes). Stereolithography (STL) files were then digitally sliced and converted to print path in G-code (3D Slicer). The converted and optimized G-code were then 3D printed with a multi-material Fused Deposition Modeling (FDM) 3D Printer (System 30M, Hyrel 3D). PLA and thermoplastic polyurethane filaments (NinjaTek NinjaFlex® 85A) with a diameter of 1.75 mm were used to create the stiff and elastomeric components respectively. The 3D printed GRA were embedded with stainless steel imaging probes (1 mm beads) to enable X-ray visualization of the printed device inside the gastric cavity (see inset FIG. 3A).

Control device fabrication: Control device ("head") of FIG. 3C was 3D printed with the same procedure as GRA (described previously) but with the gastric residence architecture ("arms") removed. The converted and optimized G-code were then 3D printed with a multi-material Fused Deposition Modeling (FDM) 3D Printer (System Hyrel 3D). PLA with a diameter of 1.75 mm was used to create the structure. Every control device was then embedded with three stainless steel imaging probes in a row (1 mm beads), spaced approximately 4 mm apart, to enable X-ray visualization of the printed device inside the gastric cavity (see inset of FIG. 3C).

Gastric Residence Electronics (GRE) fabrication: GRE was 3D printed with the same procedure as GRA (described previously) but with a CAD model integrated with electronics and batteries as shown in FIG. 2H. A 2.4 GHz Bluetooth wireless electronics board (Texas Instruments) and coin cell batteries were assembled and integrated with the 3D printed GRA structure. Epoxy (3M United States) and conductive traces were 3D printed with a custom-built 3D printer (AGS 15000, Aerotech Inc.). The 3D printer dispensing was modulated with a digital pneumatic regulator (Ultimus V High Precision Dispenser, EFD). Localized heating was applied to the 3D printed PLA with a solder iron to seal remaining gap of the 3D printed parts.

In vivo experiments: In vivo porcine studies were performed in female Yorkshire pigs aged between four and eight months and weighing approximately 35-58 kg. In vivo experiments were not blinded or randomized. Prior to endoscopy or administration of the prototypes the animals were fasted overnight immediately prior to the procedure. On the day of the procedure for the endoscopic characterization and deployment studies the animals were anesthetized with intramuscular injections of Telazol (tiletamine/zolazepam, 5 mg/kg), xylazine (2 mg/kg), and atropine (0.04 mg/kg), the pigs were intubated and maintained on inhaled isoflurane (1-3%). The esophagus was intubated with an esophageal overtube (US Endoscopy). The prototypes were delivered directly to the stomach through the overtube using the endoscope to pass the prototypes. Animals were radiographed periodically to assess prototype location. A total of ten stomach-deposited devices were evaluated in ten separate pig experiments (three for control, four for GRA and three for GRE), see FIG. 2G. Animals were monitored twice daily for changes in fecal output, abdominal distension, lethargy, inappetence, and any signs of discomfort. There were no abnormal clinical findings in any of the animals dosed with the device.

Wireless performance: To characterize the wireless electronics performance, the RSSI strength of seven devices were first measured in ambient conditions within the range of 210 cm with a smart phone. To characterize the RSSI strength of the device in vivo, the device was delivered to the stomach of a Yorkshire pig (51 kg) as described in the procedure earlier. The RSSI was measured with an Android tablet relative to the abdominal surface of the pig at three orthogonal directions. Similarly, the device is delivered to the stomach of a pig as described earlier to evaluate the performance of bilateral communications by performing temperature measurement in vivo (FIG. 4C). Lifetime optimization and characterization: To characterize the lifetime of GRE, the devices were configured to communication protocol (advertisement, connection) and to perform temperature measurement requested by an Android platform (Android 5.0, Google). The maximum operational lifetime were determined from the collected packets for advertisement and connection experiments. Specifically, for the connection test, GRE is configured to maintain Bluetooth connection at a distance of 1.2 m from the central device with the following connection parameters: "Connection Interval" of 240 ms, a "Slave latency" setting of 49. For the advertisement test, GRE is configured to advertise at 10 seconds interval and the packets are measured accordingly to determine the lifetime. For temperature measurement test, a customized Android program is built (Android Studio, Google) to seek and establish connection based on the specified MAC address of the GRE, initiate temperature measurement command at GRE, transmit and store temperature data, disconnect the device before repeating the cycle at a prescribed measurement interval. Long-term in vitro temperature measurements (FIG. 4D) were performed in an incubator at 37° C. at 100 RPM with a measurement interval of 1 hour. The maximum operational lifetime was calculated from the time-point of the collected temperature readings.

Doxycycline controlled release formulation: To prepare sustained release formulations of doxycycline, doxycycline hyclate (20% by weight) and poly(ε-caprolactone) (37 k Da) (80% by weight) were weighed in a glass vial. The glass vial was then placed in a convection oven and heated to 90° C. to melt the polymer. Once the polymer melted, the contents of the vial were mixed vigorously to evenly distribute the drug powder. The mixture was placed in the oven again, and upon melting was transferred into drug reservoirs. The drug reservoirs were weighed before filling the formulation and after filling to obtain the amount of drug loaded.

In vitro drug release of doxycycline: To analyze drug release from the sustained release doxycycline formulation, the formulations synthesized above were placed in 25 mL simulated gastric fluid (SGF) in a shaker incubator 37 ° C. and 100 RPM. At various times, a part of the release medium was aliquoted and frozen to −20° C. until further characterization. The rest of the release media was discarded and replaced with fresh media. The study was carried out for one week. On completion of the study, drug concentration in the release media aliquoted at various times was determined using high performance liquid chromatography (HPLC). HPLC was performed on an Agilent 1260 Infinity HPLC system. Chromatographic separation was carried out on an AdvanceBio RP-mAb SB-C8 column (4.6×100 mm, 3.5 m particle size) placed at 55 ° C. The mobile phase consisted of a mixture of 20 mM potassium phosphate buffer (pH 6) (60%) and acetonitrile (40%). The mobile phase was flown at 0.85 mL/min for an HPLC run time of 4 minutes. For each analysis 5 μL sample was injected on to the column, and UV absorbance was monitored at $\lambda_{max}$=350 nm.

3D printable levonorgestrel controlled release formulation: The levonorgestrel release formulation combined 30% of levonorgestrel (Astatech) with 70% of PDMS (Dow Corning) by mass in a homogeneous viscous suspension. The mixture was printed into the 3D printed drug reservoirs and solidified in a convection oven overnight. In vitro drug release of levonorgestrel: Drug release from 3D printed formulations of levonorgestrel were tested in 25 mL of SGF in a shaker incubator at 37 ° C. and 100 RPM. The remaining steps of the analysis was performed by a method identical to the one described for doxycycline. For HPLC analysis of levonorgestrel, a Poroshell 120, EC-C18, 4.6×50 mm column with 2.7 μm particle size was used. The column was maintained at 50° C. A gradient method was developed and the mobile phase consisted of water and acetonitrile. The mobile phase started as 100% aqueous at time zero, and was changed linearly to 100% organic phase over two minutes. The composition was held at 100% organic phase for the next 2.5 minutes, and then changed back 100% aqueous phase over the next 0.1 minutes. This gave a total run time of 4.6 minutes, followed by a post-time of 1.25 minutes. Detection was carried out at 250 nm.

In vivo long-term temperature monitoring: In vivo experiments were conducted according to the procedure described earlier. For long-term temperature monitoring, the pig was left to move around freely in the enclosure with an area of 1.52 m×1.52 m. Android tablets were placed 1.49 m above the ground to prevent disruption. The device was configured to advertise at eight seconds advertisement interval. Two tablets were configured to collect advertised packets to assess the electronics lifetime of the device (FIG. 5C). An additional tablet was dedicated to establish bilateral connection with GRE to measure core-temperature at a minimum interval of an hour (FIG. 5D).

Figure 6:
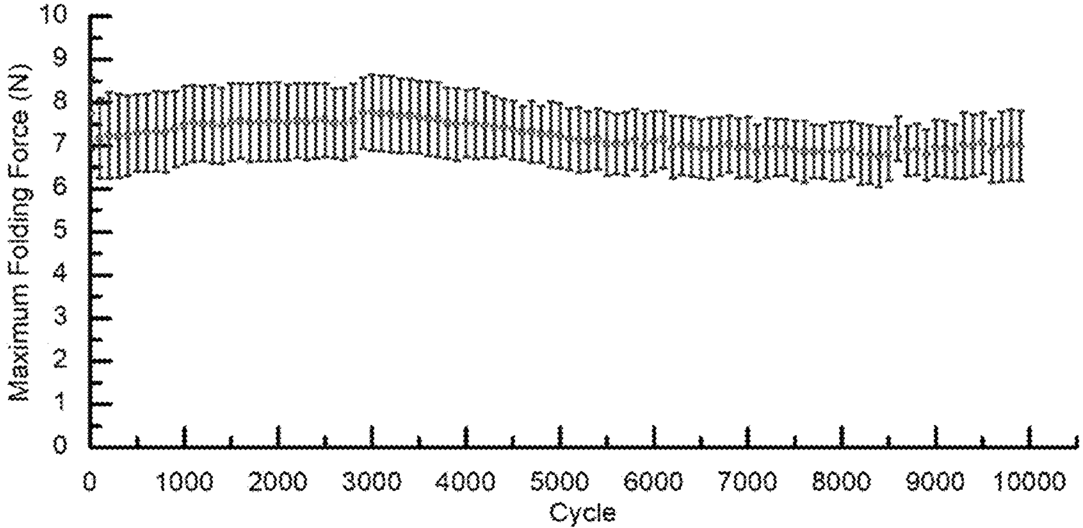
FIG. 6 shows a plot of the maximum folding force measured with funnel test apparatus to simulate the passage of GRA through pylorus, according to one set of embodiments. The measurement was repeated for 10000 cycles to evaluate the fatigue properties. Note that only 1 out of 100 points is plotted in this graph to clearly illustrate the standard deviation.

GRA Folding Force Measurement:

Funnel test apparatus was used to simulate the passage of GRA through the pylorus. In these experiments, the GRA prototype was pushed by an aluminum rod in a mechanical tester (Instron) to a maximum displacement of 13 mm and the maximum folding force were measured. As shown in FIG. 6, the folding force evaluated with GRA ranges from an average of 7.7 N (at the first cycle) to 7.0 N (after 10000 cycles). GRA also maintained the folding forces after 10000 cycles, with a relatively smaller degree of reduction of folding force.

PCL-PLA GRA: The ability to incorporate PCL-based polyurethane by first co-printing PLA with water-soluble polyvinyl alcohol (PVA) as a supporting structure was demonstrated. 3D Computer Aided Design (CAD) models of GRA as shown in FIG. 3A were first created with Solidworks 2016 (Dassault Systemes) as described previously, with the exception of modifying of co-printing with PVA instead of thermoplastic polyurethane (orange region of the FIG. 3A). Stereolithography (STL) files were then digitally sliced and converted to print path in G-code (3D Slicer). The converted and optimized G-code were then 3D printed with a multi-material Fused Deposition Modeling (FDM) 3D Printer (Ultimaker 3, Ultimaker). PLA and PVA filaments (Ultimaker) with a diameter of 2.85 mm were used to create the stiff and supporting components respectively where the PVA is then removed with water. PCL elastomer is synthesized by first mixing of a 6:1.3:0.027:9.5 molar ratio of PCL diol (MW, 530, Sigma Aldrich), PCL triol (MW, 900, Sigma Aldrich), linear PCL (MW, 45,000, Sigma Aldrich), and hexamethylene diisocyanate (Sigma Aldrich). The prepolymer is then casted into the removed PVA structure (core region of the FIG. 3A) of the 3D printed model rested on a negative mold to create the PCL-PLA based GRA structure. The PCL-PLA GRA structure demonstrates a folding force from an average of 6.7 N (at the first cycle) to 6.5 N (after 3000 cycles), as described in FIG. 7. This is in the same order as the folding force described for GRA at FIG. 6. The folding force decreases from 6.5 N after 3000 cycles to 3.1 N after 5980 cycles, which is due to the weakening and subsequently a fracture of one of the gastric residence arm. This is likely to be due to crack propagated from the microscopic bubble in the casted PCL elastomer. Future work can improve the materials synthesis process to improve the fatigue resistance of the device, for instance by developing a PCL elastomer 3D printing strategy to replace the casting process. In summary, it was shown that the fabrication procedure of GRA and GRE can be modified to incorporate thermoset plastic that cannot be directly 3D printed through FDM. This, for instance, can potentially enable the incorporation of FDA-approved materials and novel responsive material such as enteric polymers that can further minimize potential clinical complications.

Remote triggering demonstrations: Two proof-of-concept experiments were performed in vivo to demonstrate the ability to achieve remote triggering with GRE in the stomach of a large animal model. Specifically, electroactive adhesive was developed to achieve GRA separation from electronics as well as remote-delivery of drugs.

Synthesis of electroactive adhesive: First, a low melting temperature electrically conductive nanocomposite was synthesized. Specifically, a poly(ε-caprolactone) (Sigma Aldrich) and 10 wt % carbon nanotubes (Sigma Aldrich) are mixed with twin-screw micro-compounding (Xplore™ Instruments, Netherlands) to create a 3D printable filament with an average diameter of 1.75 mm and an electrical conductivity of 100 $Sm^{-1}$. The electroactive adhesive was electrically connected to a microcontroller switch in the GRE via printed conductive traces. The electroactive adhesive was used to compress a spring with the 3D printed PLA structures. Upon wireless triggering with Android tablet, Joule heating would melt the composite matrix to weaken the adhesive strength, allowing the stored elastic energy in the spring to cause structural separation. It was shown that such triggering can be achieved in vivo in the gastric cavity, as shown in the endoscopy image sequences.

(1) In vivo triggered GRA separation: To demonstrate the ability to achieve device separation, a GRA was bonded with electroactive adhesive to a "head" of 3D printed GRE. The device was delivered to the stomach of a pig. To help the capturing of the separation process, the GRA arms were tied. As describe in FIG. 8A, the device was initially intact. The separation is then triggered via an Android tablet where the GRA was separated after a minute. A slight movement of the separated structure shows that GRA was completed detached from the "head" of the GRE. FIG. 8C shows the separated device where the compression system (an embedded spring) can be observed.

Figures 9A, 9B, 9C:
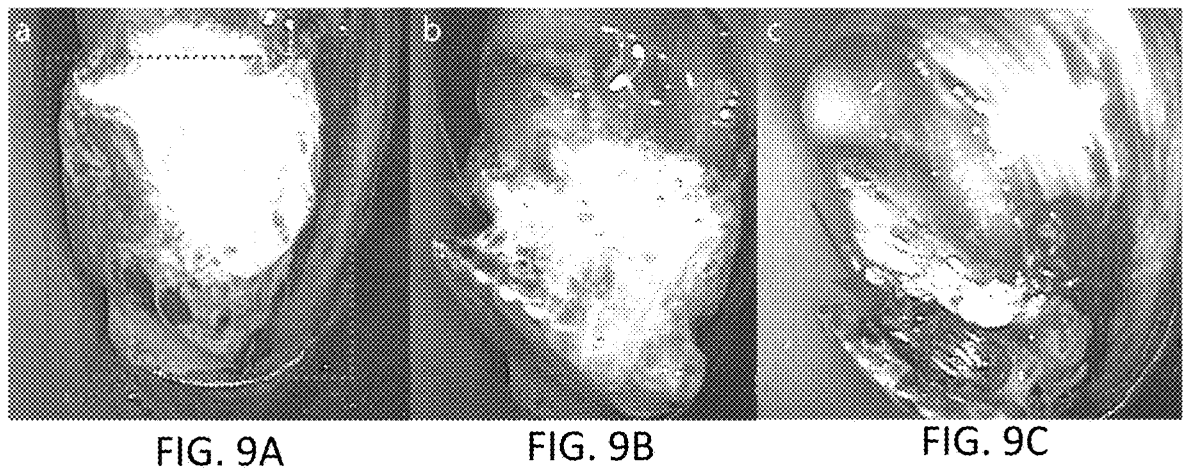
FIGS. 9A-9C show photographs of in vivo wireless triggerable release of drug-reservoir cover, according to one set of embodiments (FIG. 9A) Endoscopy images show the electractive drug delivery module (green dashed-line box) prior to triggering. Mucous films from the stomach covers reservoir.

(2) In vivo wireless triggerable release of drug-reservoir cover: Gold, which is otherwise inert in acidic environment, can be electrochemically corroded by shifting the electrochemical potential. It was previously shown that using gold as the drug release membrane, ingestible electronics can be used to power the release of micro-gram of model drug (methylene blue) in a reservoir (2 mm×1 mm×1.5 mm) that is sealed with a 300 nm thick gold membrane. During corrosion, the maximum power consumption required is 0.8 mW, which is well within the maximum power affordable by the GRE system (45 mW). To demonstrate the ability to achieve wireless large volume drug delivery, a 3D printed PLA drug window (4 mm×4 mm×0.5 mm) encapsulate the doxycycline powder reservoir 3D printed at the "head" of 3D printed GRE where the electroactive adhesive compressed a spring. As shown in FIG. 9A, the device was delivered to the stomach of a pig with procedure as described earlier (see "In vivo experiments" at Experiment Methods). Upon triggering, the Joule heating of the electroactive adhesive causes the release of the reservoir cover, allowing the infiltration of gastric fluid to dissolve the encapsulated drugs as shown in FIG. 9B. It is noted that the triggered opening of the reservoir cover was successful despite of the mucosal coverage on the delivery site. (See the attached Supplementary Videos). FIG. 9C shows the compression system after the mucous covering the triggered well was removed by injecting water through endoscope. This experiment was repeated with two-different pigs with two other devices and were all successful. It is hypothesized that the infiltration of gastric fluid into the opened drug cover will dissolve the water-soluble doxycycline. Here, the ability to achieve the wireless release of drug-reservoir cover was demonstrated. Such system should be compatible to store ingestible pills for delivery.

In summary, the ability to achieve on-demand mechanical and structural changes with the GRE chipset was demonstrated, which can be used for releasing drug-containing reservoir in vivo and other potential applications.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A gastric resident structure, comprising:

an elastic core;

three or more polymeric arms extending radially from the elastic core; and a separate degradable linker coupling at least one of the three or more polymeric arms to the elastic core, wherein at least one of the three or more polymeric arms comprises an electronic component, and wherein at least one of the polymeric arms is configured to separate from the electronic component.

2. A gastric resident structure configured for oral administration, comprising:

an elastic core;

three or more polymeric arms extending radially from the elastic core; and an electronic component, wherein at least one of the three or more polymeric arms comprises an electronic component, wherein the gastric resident structure is configured such that it is retained at a location internally of a subject for at least about 24 hours, wherein the location internally of the subject is a stomach of the subject, and wherein at least one of the polymeric arms is configured to separate from the electronic component.

3. A gastric resident structure configured for transmission of a signal extra-corporeally, comprising:

an elastic core, three or more polymeric arms extending radially from the elastic core, an electronic component comprising a wireless transmitter, wherein at least one of the three or more polymeric arms comprises the electronic component, wherein the gastric resident structure is configured such that it is administered orally and retained at a location internal to a subject adjacent the pylorus of a subject for at least about 24 hours, wherein the location internally of the subject is a stomach of the subject, wherein the wireless transmitter is configured to transmit a signal from the location internal to the subject to a receiver positioned extracorporeal of the subject, and wherein at least one of the polymeric arms is configured to separate from the electronic component.

4. The gastric resident structure as in claim 1, comprising a pharmaceutical agent associated with the electronic component.

5. The gastric resident structure as in claim 4, wherein at least a portion of the pharmaceutical agent is configured to be released upon a signal received from the electronic component.

6. A method for delivering an electronic component to a subject, comprising:

administering orally, to a subject, a gastric resident structure comprising an electronic component such that the electronic component is retained at a location internal to the subject for at least about 24 hours, wherein the location internal to the subject is a stomach of the subject, wherein the gastric resident structure comprises an elastic core, three or more polymeric arms extending radially from the elastic core, wherein one of the three or more polymeric arms comprises the electronic component, and wherein at least one of the polymeric arms is configured to separate from the electronic component.

7. The method as in claim 6, wherein the gastric resident structure comprises a degradable linker.

8. The method as in claim 7, further comprising removing the electronic component from the location internal to the subject by degrading the degradable linker.

9. The method as in claim 8, wherein degrading the degradable linker comprises applying, via the electronic component, a voltage to the degradable linker.

10. The method as in claim 9, wherein the degradable linker comprises a plurality of carbonaceous particles, carbon nanotubes, and/or conductive particles.

11. The gastric resident structure as in claim 2, wherein the location internal to the subject is the stomach.

12. The gastric resident structure as in claim 2, wherein the location internal to the subject is proximate the pylorus.

13. The gastric resident structure as in claim 1, wherein the degradable linker comprises a plurality of carbonaceous particles, carbon nanotubes, and/or conductive particles.

14. The gastric resident structure as in claim 1, wherein the electronic component is configured to apply a voltage to the degradable linker.

15. The gastric resident structure as in claim 1, wherein the degradable linker is configured to degrade in the presence of a voltage.

16. The gastric resident structure as in claim 1, wherein the degradable linker is configured to degrade in the presence of a generated increase in temperature.

17. The gastric resident structure as in claim 1, wherein the degradable linker degrades, dissolves, disassociates, or mechanically weakens in a gastric environment which results in loss of retention shape integrity and passage out of a gastric cavity.

18. The gastric resident structure as in claim 1, wherein the three or more polymeric arms are configured to maintain structural integrity during a residence period of the gastric resident structure.

19. The gastric resident structure as in claim 1, further comprising a containing structure.

20. The gastric resident structure as in claim 19, wherein the gastric resident structure is constructed and arranged to have a first configuration when contained within the containing structure and a second configuration after release from the containing structure.

21. The gastric resident structure as in claim 1, wherein the electronic component comprises a wireless transmitter.

22. The gastric resident structure as in claim 1, wherein the electronic component comprises a pharmaceutical agent configured for release at a location internal to a subject.

23. The gastric resident structure as in claim 19, wherein the gastric resident structure is constructed and arranged to undergo elastic recoil upon release from the containing structure, the gastric resident structure having a first configuration when contained within the containing structure and a second configuration after release from the containing structure.

* * * * *